US011299822B2

(12) United States Patent
Zussman et al.

(10) Patent No.: US 11,299,822 B2
(45) Date of Patent: *Apr. 12, 2022

(54) METHOD OF PRODUCING A MICROTUBE

(71) Applicant: TECHNION RESEARCH & DEVELOPMENT FOUNDATION LTD., Haifa (IL)

(72) Inventors: Eyal Zussman, Haifa (IL); Yael Dror, Misgav (IL); Wael Salalha, Beit-Jann (IL); Ron Avrahami, Kiryat-Tivon (IL)

(73) Assignee: TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/446,228

(22) Filed: Mar. 1, 2017

(65) Prior Publication Data

US 2017/0175296 A1 Jun. 22, 2017

Related U.S. Application Data

(63) Continuation of application No. 12/311,601, filed as application No. PCT/IB2007/054001 on Oct. 2, 2007, now abandoned.

(Continued)

(51) Int. Cl.
*D01D 5/00* (2006.01)
*A61F 2/06* (2013.01)
(Continued)

(52) U.S. Cl.
CPC .............. *D01D 5/0069* (2013.01); *A61F 2/06* (2013.01); *A61L 27/34* (2013.01); *A61L 27/507* (2013.01);
(Continued)

(58) Field of Classification Search
CPC ...... B29C 48/16; B29C 48/335; D01D 5/003; D01D 5/0038; D01D 5/0046; D01D 5/0069; D01D 5/24
(Continued)

(56) References Cited

U.S. PATENT DOCUMENTS 4,921,475 A 5/1990 Sibalis
5,209,734 A 5/1993 Hurley et al.
(Continued)

FOREIGN PATENT DOCUMENTS

AU 2007303821 5/2009
CN 1799649 7/2006
(Continued)

OTHER PUBLICATIONS

Bognitzki, et al., "Polymer, Metal, and Hybrid Nano- and Mesotubes by Coating Degradable Polymer Template Fibers (TUFT Process)", Advanced Materials, vol. 12 No. 9: 637-640, 2000.
(Continued)

*Primary Examiner* — Leo B Tentoni
(74) *Attorney, Agent, or Firm* — The Roy Gross Law Firm, LLC; Roy Gross

(57) ABSTRACT

A method of producing a microtube is provided. The method comprising co-electrospinning two polymeric solutions through co-axial capillaries to thereby produce the microtube, wherein a first polymeric solution of the two polymeric solutions is for forming a shell of the microtube and a second polymeric solution of the two polymeric solutions is for forming a coat over an internal surface of the shell, the first polymeric solution is selected solidifying faster than the second polymeric solution and a solvent of the second polymeric solution is selected incapable of dissolving the first polymeric solution. Also provided are electrospun microtubes.

16 Claims, 12 Drawing Sheets
(6 of 12 Drawing Sheet(s) Filed in Color)

Related U.S. Application Data

(60) Provisional application No. 60/849,442, filed on Oct. 5, 2006.

(51) Int. Cl.
| | |
|---|---|
| *D01D 5/24* | (2006.01) |
| *D01F 8/04* | (2006.01) |
| *A61L 31/10* | (2006.01) |
| *D01D 5/247* | (2006.01) |
| *A61L 27/34* | (2006.01) |
| *A61L 27/50* | (2006.01) |
| *A61L 27/56* | (2006.01) |
| *D01F 8/06* | (2006.01) |
| *B29C 48/16* | (2019.01) |
| *B29C 48/335* | (2019.01) |

(52) U.S. Cl.
CPC .............. *A61L 27/56* (2013.01); *A61L 31/10* (2013.01); *D01D 5/003* (2013.01); *D01D 5/0038* (2013.01); *D01D 5/0046* (2013.01); *D01D 5/24* (2013.01); *D01D 5/247* (2013.01); *D01F 8/04* (2013.01); *D01F 8/06* (2013.01); *A61F 2240/001* (2013.01); *B29C 48/16* (2019.02); *B29C 48/335* (2019.02); *D10B 2509/00* (2013.01); *Y10T 428/2935* (2015.01)

(58) Field of Classification Search
USPC .... 264/10, 171.26, 171.28, 209.1, 464, 465, 264/466, 484
See application file for complete search history.

(56) References Cited

U.S. PATENT DOCUMENTS

| | | | |
|---|---|---|---|
| 5,688,501 | A | 11/1997 | Merril et al. |
| 5,795,340 | A | 8/1998 | Lang |
| 6,537,195 | B2 | 3/2003 | Forman |
| 6,537,241 | B1 | 3/2003 | Odland |
| 7,066,922 | B2 | 6/2006 | Angel et al. |
| 10,023,474 | B2 * | 7/2018 | Ben Dror ............... C02F 1/681 |
| 2001/0014394 | A1 | 8/2001 | Soane et al. |
| 2001/0034503 | A1 | 10/2001 | Mehier |
| 2003/0026985 | A1 | 2/2003 | Greiner et al. |
| 2003/0098518 | A1 | 5/2003 | Averdung et al. |
| 2003/0135158 | A1 | 7/2003 | Gonnelli |
| 2003/0139727 | A1 | 7/2003 | Angel et al. |
| 2004/0018226 | A1 | 1/2004 | Wnek et al. |
| 2004/0030377 | A1 | 2/2004 | Dubson et al. |
| 2004/0086591 | A1 | 5/2004 | Vollrath et al. |
| 2004/0147903 | A1 | 7/2004 | Latini |
| 2004/0223954 | A1 | 11/2004 | Bruessow et al. |
| 2005/0180992 | A1 | 8/2005 | Belcher et al. |
| 2006/0119015 | A1 | 6/2006 | Wehrspohn et al. |
| 2006/0200232 | A1 | 9/2006 | Phaneuf et al. |
| 2006/0226580 | A1 | 10/2006 | Xia et al. |
| 2006/0228435 | A1 | 10/2006 | Andrady et al. |
| 2009/0061496 | A1 | 3/2009 | Kuhn et al. |
| 2010/0129656 | A1 | 5/2010 | Zussman et al. |
| 2010/0193550 | A1 | 8/2010 | Bittner |
| 2010/0303881 | A1 | 12/2010 | Hoke et al. |
| 2011/0081394 | A1 | 4/2011 | Zussman et al. |

FOREIGN PATENT DOCUMENTS

| | | |
|---|---|---|
| EP | 2079860 | 8/2013 |
| WO | 03000381 | 1/2003 |
| WO | 2006019293 | 2/2006 |
| WO | 2006108809 | 10/2006 |
| WO | 2008041183 | 4/2008 |
| WO | 2009104174 | 8/2009 |
| WO | 2009104175 | 8/2009 |
| WO | 2009104176 | 8/2009 |

OTHER PUBLICATIONS

Caruso, et al., "Titanium Dioxide Tubes from Sol-Gel Coating of Electrospun Polymer Fibers", Advanced Materials, vol. 13 No. 20: 1577-1579, Oct. 16, 2001.

Dror, et al., "One-Step Production of Polymeric Microtubes by Co-Electrospinning", Small, XP002497054, 3(6): 1064-1073, Jun. 4, 2007.

Dror, et al., "Viable Encapsulation of Enzymes in Biodegradable Tubular Structures", Macromolecules 41: 4187-4192, 2008.

He, et al., "Recent Development of the Nanocomposites Prepared by Coaxial Jet Technology", Acta Materiae Compositae Sinica, 22(6): 1-8, Dec. 2005.

Huang, et al., "Encapsulating Drugs in Biodegradable Ultrafine Fibers Through Co-Axial Electrospinning", Journal of Biomedical Materials Research, Part A, 77A: 169-179, 169, 2006.

Jiang, et al., "A Facile Technique to Prepare Biodegradable Coaxial Electrospun Nanofibers for Controlled Release of Bioactive Agents", Journal of Controlled Release, 108(2-3): 237-243, Nov. 28, 2005.

Jiang, et al., "Modulation of Protein Release from Biodegradable Core-Shell Structured Fibers Prepared by Coaxial Electrospinning", Journal of Biomedical Materials Research Part B: Applied Biomaterials, 79B: 50-57, 2006.

Kim, et al., "Controlled protein release from electrospun biodegradable fiber mesh composed of poly(e-caprolactone) and poly(ethylene oxide)", International Journal of Pharmaceutics, vol. 338: 276-283, 2007.

Larsson, et al., "Detection of Number and Viability of E. Coli and A. Hydrophila With FISH Technique", Techneau, p. 1-30, Apr. 30, 2008.

Lee, et al., "Virus-Based Fabrication of Micro- and Nanofibers Using Electrospinning", NanoLetters, vol. 4 No. 3: 387-390, 2004.

Li, et al., "Direct Fabrication of Composite and Ceramic Hollow Nanofibers by Electrospinning", Nano Letters, vol. 4 No. 5: 933-938, 2004.

Li, et al., "Electrospinning of Nanofibers: Reinventing the Wheel?", Advanced Materials, vol. 16 No. 14: 1151-1170, Jul. 19, 2004.

Xinsong, et al., "Nano-Porous Ultra-High Specific Surface Ultrafine Fibers", Chinese Science Bulletin, vol. 49 No. 22: 2368-2371, Nov. 2004.

Li, et al., "Use of Electrospinning to Directly Fabricate Hollow Nanofibers with Functionalized Inner and Outer Surfaces", Small, 1(1): 83-86, Jan. 1, 2005.

Li, et al., "Electrospinning: A Simple and Versatile Technique for Producing Ceramic Nanofibers and Nanotubes", Journal of the American Ceramic Society, vol. 89 No. 6: 1861-1869, 2006.

Loscertales, et al., "Micro/Nano Encapsulation via Electrified Coaxial Liquid Jets", Science, vol. 295: 1695-1698, Mar. 16, 2002.

Loscertales, et al., "Electrically Forced Coaxial Nanojets for One-Step Hollow Nanofiber Design", Journal of the American Chemical Society, vol. 126: 5376-5377, 2004.

McCann, et al., "Electrospinning of Nanofibers With Core-Sheath, Hollow, or Porous Structures", Journal of Materials Chemistry, vol. 15: 735-738, 2005.

Reneker, et al., "Electrospinning of Nanofibers from Polymer Solutions and Melts", Advances in Applied Mechanics, vol. 41: 43-195, 345-346, 2007.

Reznik, et al., "Evolution of a Compound Droplet attached to a Core-Shell Nozzle Under the Action of a Strong Electric Field", Physics of Fluids, vol. 18: 062101-1-062101-13, 2006.

Salalha, et al., "Encapsulation of Bacteria and Viruses in Electrospun Nanofibres", Nanotechnology, 17: 4675-4681, 2006.

Sun, et al., "Compound Core-Shell Polymer Nanofibers by Co-Electrospinning", Advanced Materials, vol. 15 No. 22: 1929-1932, Nov. 17, 2003.

Theron, et al., "Electrostatic Field-Assisted Alignment of Electrospun Nanofibres", Nanotechnology, vol. 12: 384-390, 2001.

Xie, et al., "Ultra-High Surface Fibrous Membranes from Electrospinning of Natural Proteins: Casein and Lipase Enzyme", Journal of Materials Science, vol. 38: 2125-2133, 2003.

(56) References Cited

OTHER PUBLICATIONS

Yarin, et al., "Material Encapsulation and Transport in Core-Shell Micro/Naonofibers, Polymer and Carbon Nanotubes and Micro/Nanochannels", Journal of Materials Chemistry, vol. 17 No. 25: 2585-2599, Jul. 1, 2007.

Yee, et al., "Morphology, polymorphism behavior and molecular orientation of electrospun poly(vinylidene fluoride) fibers", Polymer, vol. 48: 512-521, 2006.

Yu, et al., "Production of Submicrometer Diameter Fibers by Two-Fluid Electrospinning", Advanced Materials, vol. 16 No. 17: 1562-1566, Sep. 3, 2004.

Zhang, et al., "Coaxial Electrospinning of (Fluorescein Isothiocyanate-Conjugated Bovine Serum Albumin)-Encapsulated Poly(e-Caprolactone) Nanofibers for Sustained Release", Biomacromolecules, vol. 7 No. 4: 1049-1057, 2006.

Zhang, et al., "Biomimetic and bioactive nanofibrous scaffolds from electrospun composite nanofibers", International Journal of Nanomedicine, vol. 2 No. 4: 623-638, 2007.

Zussman, et al., "Formation of Nanofiber Crossbars in Electrospinning", Applied Physics Letters, vol. 82 No. 6: 973-975, Feb. 10, 2003.

Zussman, et al. "Electrospun Polyacrylonitrile/Poly(methyl methacrylate)-Derived Turbostratic Carbon Micro-/Nanotubes", Advanced Materials, vol. 18: 348-353, 2006.

International Search Report and Written Opinion of the Searching Authority, International Application No. PCT/IL2009/000169, dated Sep. 29, 2009.

International Search Report and Written Opinion of the Searching Authority, International Application No. PCT/IB2007/054001, dated Oct. 14, 2008.

International Search Report and Written Opinion of the Searching Authority, International Application No. PCT/IL2009/000170, dated Sep. 30, 2009.

International Search Report and Written Opinion of the Searching Authority, International Application No. PCT/IL2009/000171, dated Sep. 29, 2009.

International Preliminary Report on Patentability, International Application No. PCT/IL2009/000171, dated Aug. 24, 2010.

International Preliminary Report on Patentability, International Application No. PCT/IL2009/000170, dated Aug. 24, 2010.

International Preliminary Report on Patentability, International Application No. PCT/IL2009/000169, dated Aug. 24, 2010.

\* cited by examiner

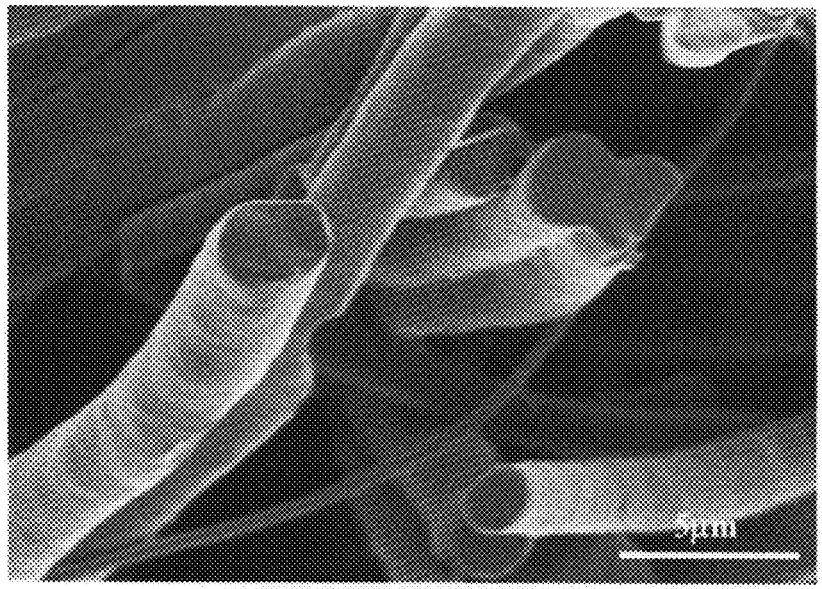
Fig. 4
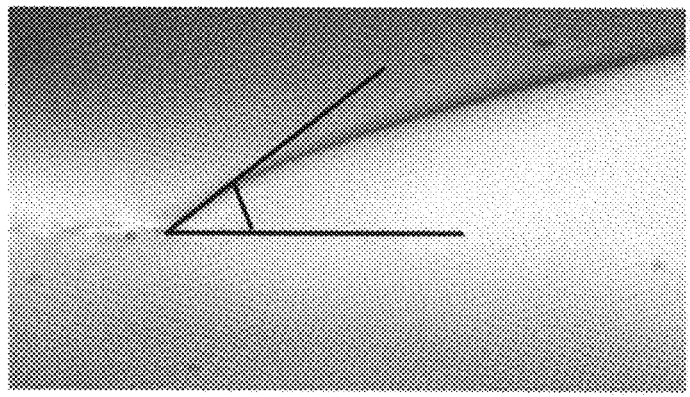 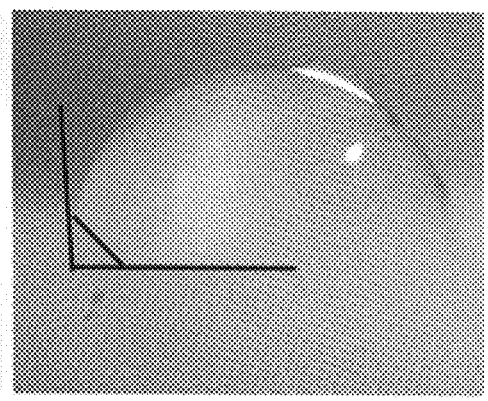
Fig. 5a　　　　　　　　　Fig. 5b

METHOD OF PRODUCING A MICROTUBE

CROSS-REFERENCE TO RELATED APPLICATIONS

This application is a continuation of U.S. Ser. No. 12/311,601 having a 371c date of Jan. 28, 2010, which is a National Phase of PCT Patent Application No. PCT/IB2007/054001 having International filing date of Oct. 2, 2007, which claims the benefit of priority of U.S. Provisional Patent Application No. 60/849,442 filed on Oct. 5, 2006. The contents of the above applications are all incorporated by reference as if fully set forth herein in their entirety.

FIELD AND BACKGROUND OF THE INVENTION

Fabrication of nanoscopic and microscopic hollow structures such as polymer tubes receives increasing attention due to the potential application of tubes in microfluidics, catalysis, drug release, nerve guidance and oxygenerators. The electrospinning process is well-known for producing nanofibers and polymeric nanofibers in particular (Reneker D H., et al., 2006; Ramakrishna S., et al., 2005; Li D, et al., 2004; PCT WO 2006/106506 to the present inventors).

There are two known approaches for fabricating tubes using electrospinning. One approach, also known as the TUFT process (Bognitzki et al. 2000) is based on using the electrospun nanofibers as templates. In this case polymeric nanofibers are produced by electrospinning and then coated by various deposition methods with a precursor material from which the tubes are made. Subsequently, the inner electrospun fiber is removed by selective dissolution or thermal degradation and tubes with nanometric and controlled inner diameter are gained. Modification of this process using the sol-gel procedure to coat the template nanofiber was employed for fabricating titanium dioxide tubes with special morphologies (Caruso et al., 2001). The second approach uses the co-electrospinning process in which two different solutions are spun simultaneously using a two co-axial capillaries spinneret to produce core-shell nanofibers (Sun Z, et al., 2003; Yu J H, et al., 2004; Huang Z M, et al., 2006; Jiang H., et al., 2005; Zhang Y Z., et al., 2006). The core is then selectively removed and hollow fibers are formed. This method was used to fabricate ceramic hollow fibers by co-electrospinning viscous mineral oil as the core and a mixture of Polyvinylpyrrolidone (PVP) and Ti(OiPr)4 in ethanol as shell (Li D., et al., 2004; Li D., et al., 2005). The mineral oil was subsequently extracted and finally, after calcination, hollow fibers made of titania were obtained. Turbostratic carbon nano-tubes were also obtained by co-electrospinning of Polyacrylonitrile (PAN)/Polymethyl methacrylate (PMMA) with a subsequent thermal degradation of the PMMA core and finally carbonization of the PAN shell (Zussman E, et al., 2006). Both of these tube fabrication approaches were mainly used to produce ceramic, carbon or metallic tubes.

Studies show that co-electrospinning of two polymeric solutions which are sufficiently viscous, spinnable and immiscible can result in solid core-shell fibers (i.e., filled fibers and not hollow fibers) (Li D., et al., 2006; Loscertales I G., et al., 2002; Loscertales I G., et al., 2004). Another study by the present inventors (Sun Z et al., 2003) showed that although core-shell nanofibers made of miscible solutions can be achieved this process is less controllable since mutual diffusion can take place in the Taylor cone and during the jet stretching.

Small blood vessels (10-2000 microns) including capillaries, arterioles and venules connect arteries to veins and provide essential functions of the circulatory system such as exchange of nutrients and gases with the tissue and distribution of blood flow. Tissue damage (e.g., Atherosclerosis diseases, ischemia diseases) due to disruption of blood flow can be corrected in the case of large arterial (4 mm-30 mm) using artificial or autologous conduits. The most common form of treatment is coronary artery bypass graft (CABG) surgery. The current used grafts have met with success, but when used in the coronary system, where diameters are 0.01 mm-2 mm, thrombotic events rapidly close them off. Hence, in many laboratories, tissue engineering moved toward engineering a blood vessel substitute that exhibit all the functional characteristics of a normal blood vessel. This requires that the engineered substitute not only be non-thrombogenic, it also must exhibit vasoactivity and possess appropriate mechanical properties.

SUMMARY OF THE INVENTION

According to one aspect of the invention there is provided a method of producing a microtube, the method comprising: co-electrospinning two polymeric solutions through co-axial capillaries to thereby produce the microtube, wherein a first polymeric solution of the two polymeric solutions is for forming a shell of the microtube and a second polymeric solution of the two polymeric solutions is for forming a coat over an internal surface of the shell, the first polymeric solution is selected solidifying faster than the second polymeric solution and a solvent of the second polymeric solution is selected incapable of dissolving the first polymeric solution.

According to another aspect of the invention there is provided a microtube comprising an electrospun shell and an electrospun coat over an internal surface of the shell.

According to further features in the embodiments of the invention described below, the electrospun shell is formed of a first polymeric solution and the electrospun coat is formed of a second polymeric solution.

According to still further features in the described embodiments the first polymeric solution solidifies faster than the second polymeric solution.

According to still further features in the described embodiments a solvent of the second polymeric solution is incapable of dissolving the first polymeric solution.

According to still further features in the described embodiments the electrospun shell comprises a polymer selected from the group consisting of: poly (e-caprolactone) (PCL), polyamide, poly(siloxane), poly(silicone), poly(ethylene), poly(vinyl pyrrolidone), poly(2-hydroxy ethylmethacrylate), poly(N-vinyl pyrrolidone), poly(methyl methacrylate), poly(vinyl alcohol), poly(acrylic acid), poly(vinyl acetate), polyacrylamide, poly(ethylene-co-vinyl acetate), poly(ethylene glycol), poly(methacrylic acid), polylactide, polyglycolide, poly(lactide-coglycolide), polyanhydride, polyorthoester, poly(carbonate), poly(acrylo nitrile), poly (ethylene oxide), polyaniline, polyvinyl carbazole, polystyrene, poly(vinyl phenol), polyhydroxyacid, poly(caprolactone), polyanhydride, polyhydroxyalkanoate, polyurethane, collagen, albumin, alginate, chitosan, starch, hyaluronic acid, and whereas the electrospun coat comprises a polymer selected from the group consisting of poly(acrylic acid), poly(vinyl acetate), polyacrylamide, poly(ethylene-co-vinyl acetate), poly(ethylene glycol), poly(methacrylic acid), polylactide polyglycolide, poly(lactide-coglycolide), polyanhydride, polyorthoester, poly(carbonate), poly(ethylene oxide), polyaniline, polyvinyl carbazole, polystyrene, poly (vinyl phenol), polyhydroxyacid, alginate, starch, hyaluronic acid.

According to still further features in the described embodiments a solvent of the first polymeric solution evaporates faster than a solvent of the second polymeric solution.

According to still further features in the described embodiments the electrospinning is effected using a rotating collector.

According to still further features in the described embodiments a solvent of the second polymeric solution is capable of evaporating through the internal surface of the shell.

According to still further features in the described embodiments the second polymeric solution is selected capable of wetting the internal surface of the shell.

According to still further features in the described embodiments a thickness of the shell is from about 100 nm to about 20 micrometer.

According to still further features in the described embodiments an internal diameter of the microtube is from about 50 nm to about 20 micrometer.

According to still further features in the described embodiments the first and the second polymeric solutions are selected from the group consisting of: 10% poly (e-caprolactone) (PCL) in chloroform ($CHCl_3$) and 20 dimethylforamide (DMF) (80:20 by weight) as the first polymeric solution and 4% poly(ethylene oxide) (PEO) in water ($H_2O$) and ethanol (60:40 by weight) as the second polymeric solution, 10% PCL in $CHCl_3$ and DMF (80:20 by weight) as the first polymeric solution and 6% PEO in $H_2O$ and ethanol (60:40 by weight) as the second polymeric solution, 9% PCL in $CHCl_3$ and DMF (90:10 by weight) as the first polymeric solution and 7% PEO in $H_2O$ as the second polymeric solution, and 10% PCL in $CHCl_3$ and DMF (800:20 by weight) as the first polymeric solution and 9% poly(vinyl alcohol) (PVA) in water and ethanol (50:50 by weight) as the second polymeric solution.

According to still further features in the described embodiments the first polymeric solution comprises polyethylene glycol (PEG).

According to still further features in the described embodiments the shell comprises pores.

According to still further features in the described embodiments the microtube is filled with a liquid.

According to still further features in the described embodiments the liquid is blood.

According to still further features in the described embodiments the first and the second polymeric solutions are biocompatible.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
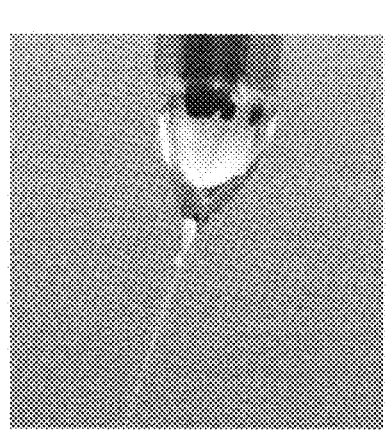
Figure 2A:
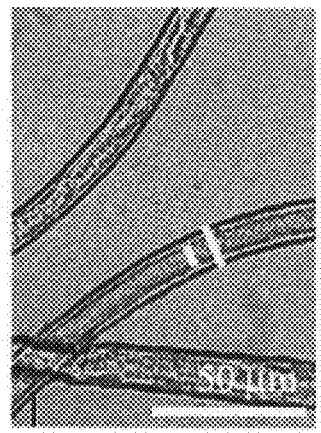
Figure 2B:
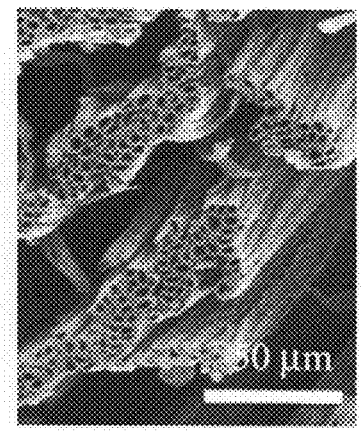
Figure 2C:
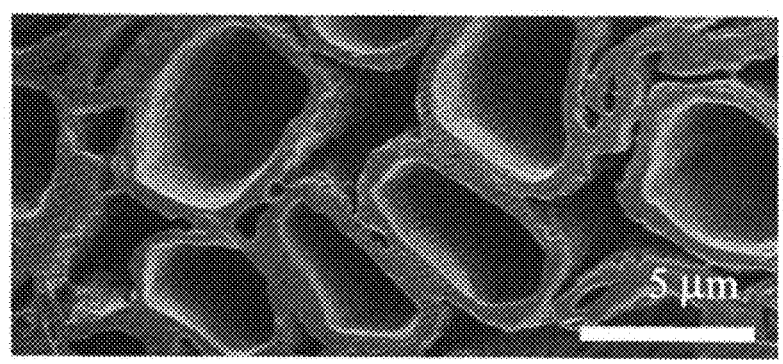
Figure 2D:
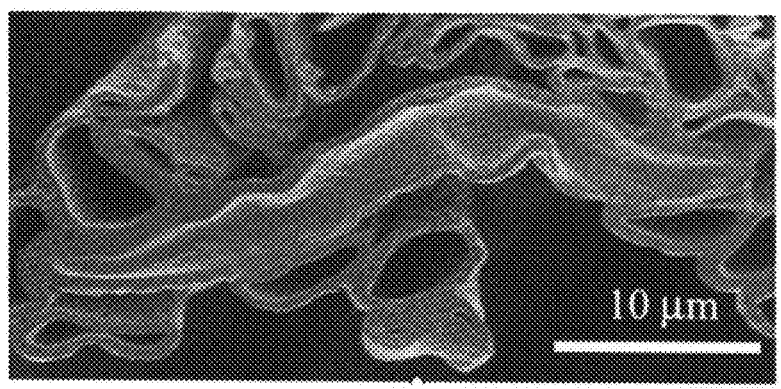
Figure 3A:
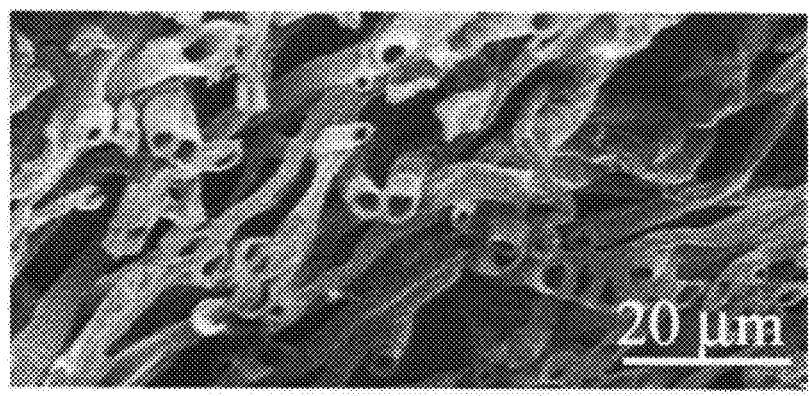
Figure 3B:
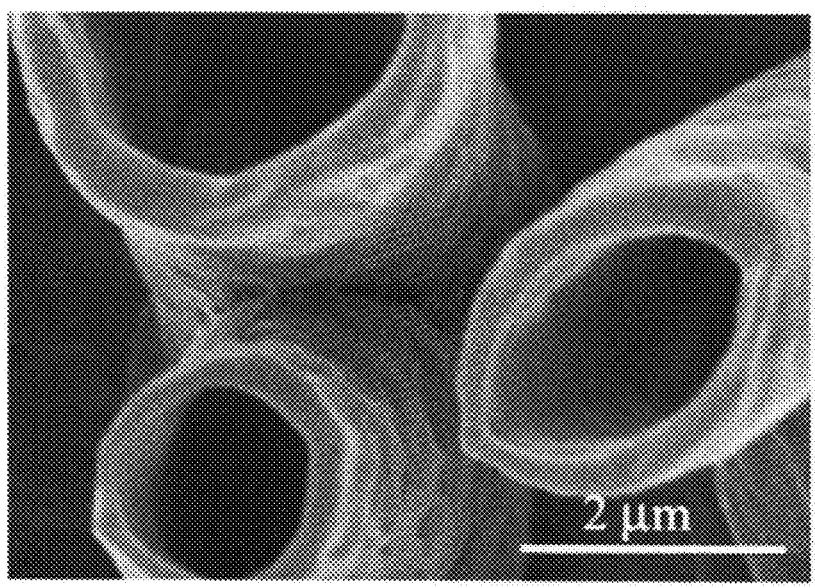
Figure 3C:
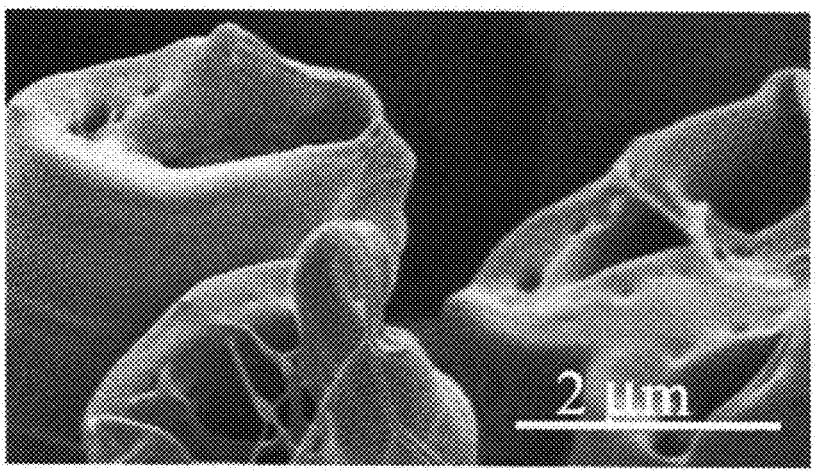

FIG. 1 is an image of a compound pendant drop of PCL solution as a shell, and PEO solution as core (shell 1, core 1 as described in Table 2 of the Examples section which follows). The white arrow points to the protrusion of the inner capillary outside the shell capillary. The black arrow points to the Gelled interface between solutions. Shell flow rate=4 ml/hour, core flow rate=0.5 ml/hour;

FIGS. 2a-d are photomicrographs of co-electrospun PCL-shell PEO-core (shell 1, core 1, as described in Table 2 of the Examples section which follows) nanofibers: FIG. 2a—light microscope (LM) micrograph; FIGS. 2b-d—HRSEM (high resolution scanning electron microscope) micrographs at different magnifications. Shell flow rate=4 ml/hour, core flow rate=0.5 ml/hour;

FIGS. 3a-c are HRSEM photomicrographs of co-electrospun fibers: FIGS. 3a-b—PCL-shell, PVA-core (shell 1, core 2, as described in Table 2 of the Examples section which follows), shell flow rate=3.5 ml/hour, core flow rate=0.5 ml/hour; FIG. 3c—PCL-shell PEO-core (shell 1, core 3, as described in Table 2 of the Examples section which follows), shell flow rate=3.5 ml/hour, core flow rate=0.5 ml/hour;

FIG. 4 is an HRSEM micrograph of fibers' cross-sections made of PCL only (at the same composition as shell 1, as described in Table 2 of the Examples section which follows)

Figure 6A:
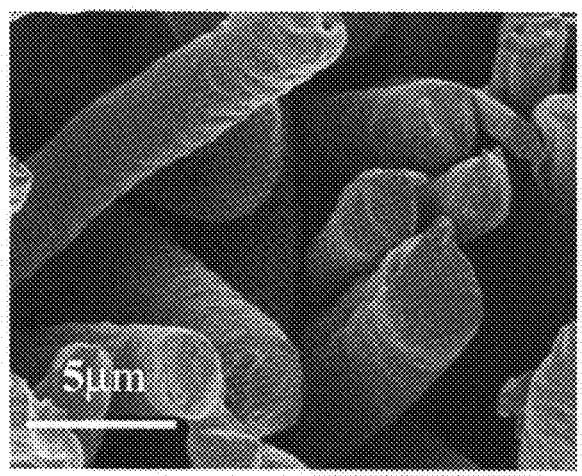
Figure 6B:
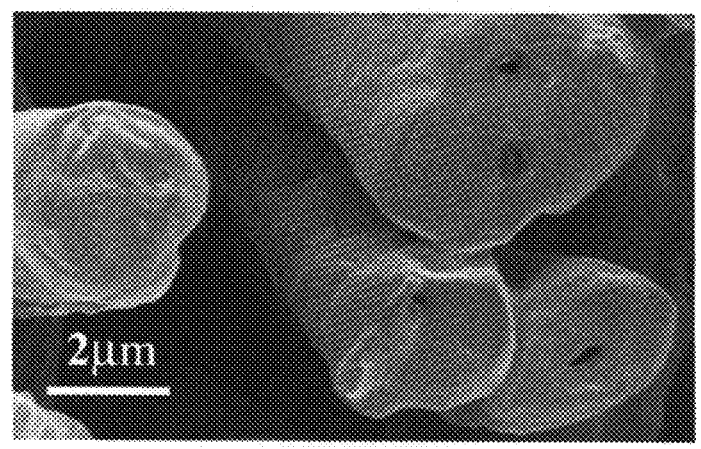
Figure 6C:
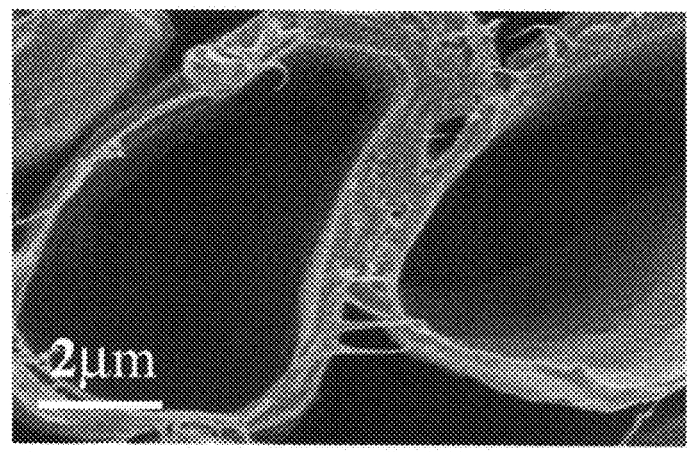

FIGS. 5a-b are images depicting contact angles: FIG. 5a—drop of PEO solution (core 1, as described in Table 2 of the Examples section which follows) on PCL film; FIG. 5b-drop of water on PCL film;

FIGS. 6a-c are HRSEM micrographs of fibers made of PCL (shell 1) PEO (core 1): FIGS. 6a-b—core 4—conductivity of 200 µS/cm, shell flow rate=3 ml/hour and core flow rate=0.3 ml/hour; FIG. 6c—core 1—conductivity of 13 µS/cm, shell flow rate=3 ml/hour, core flow rate=0.3 ml/hour (b); The core and shell polymers are described in Table 2 of the Examples section which follows.

Figure 7A:
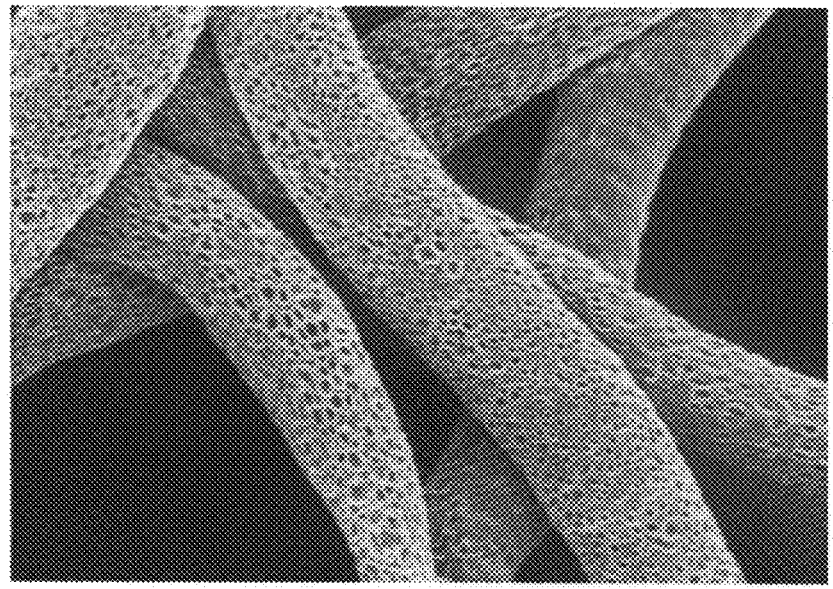
Figure 7B:
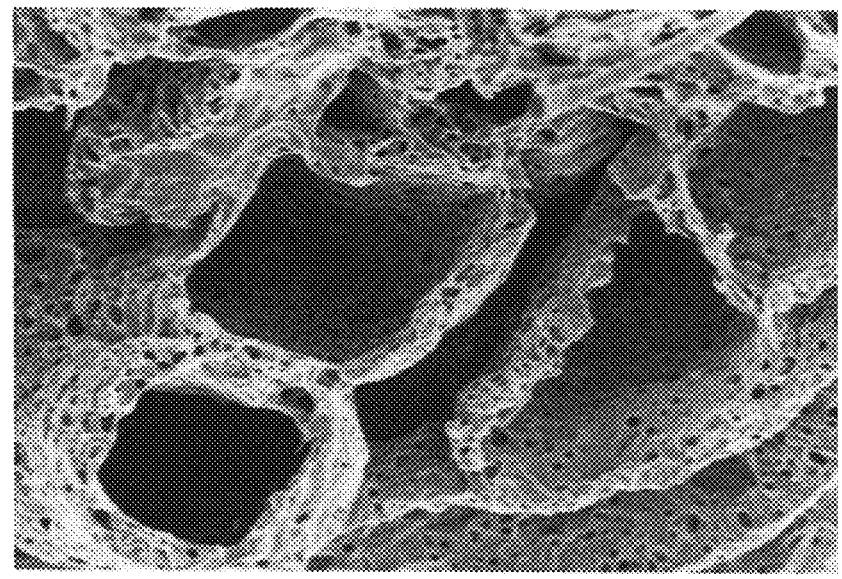

FIGS. 7a-b are HRSEM photomicrographs of extensively porous micro tubes: FIG. 7a—shell 2, core 1; FIG. 7b—shell 3, core 1; The core and shell polymers are described in Table 2 of the Examples section which follows.

Figure 8:
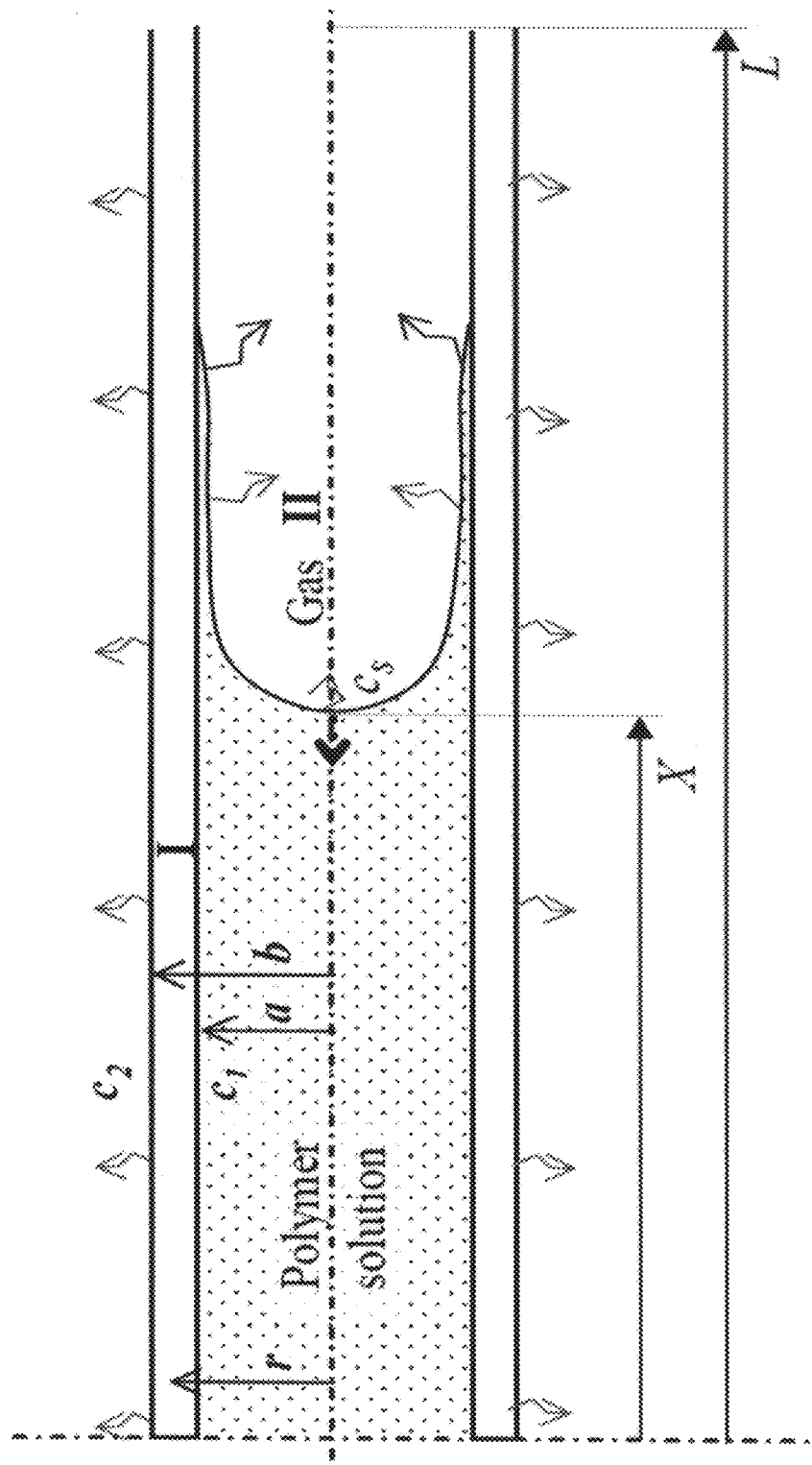
Figures 9A, 9B, 9C, 9D:
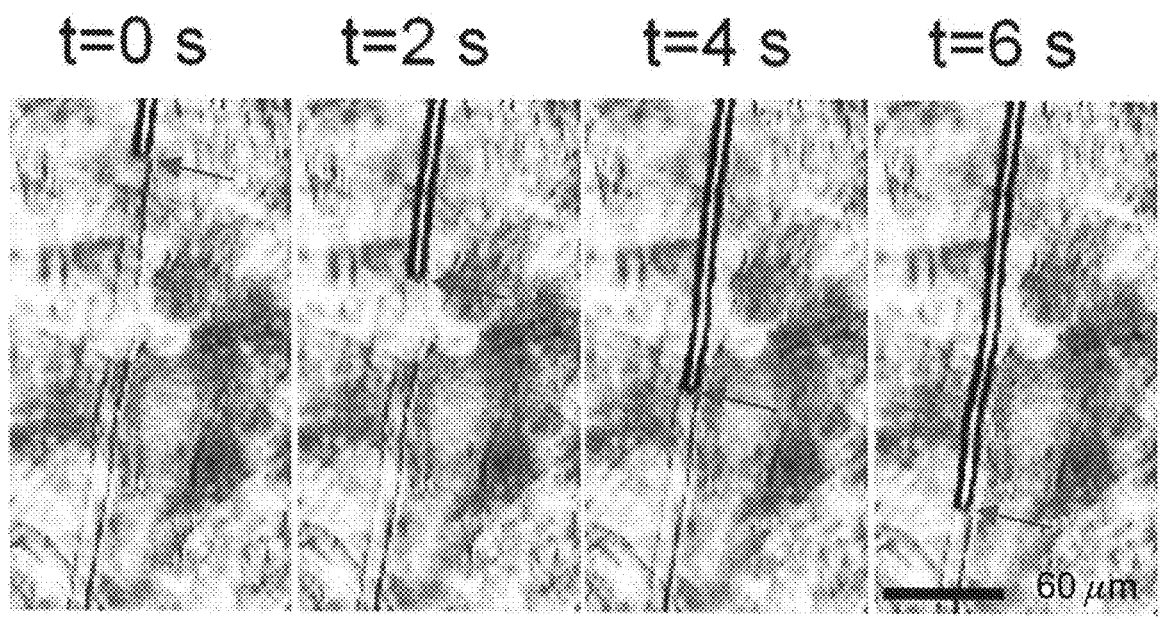
Figures 9E, 9F, 9G, 9H:
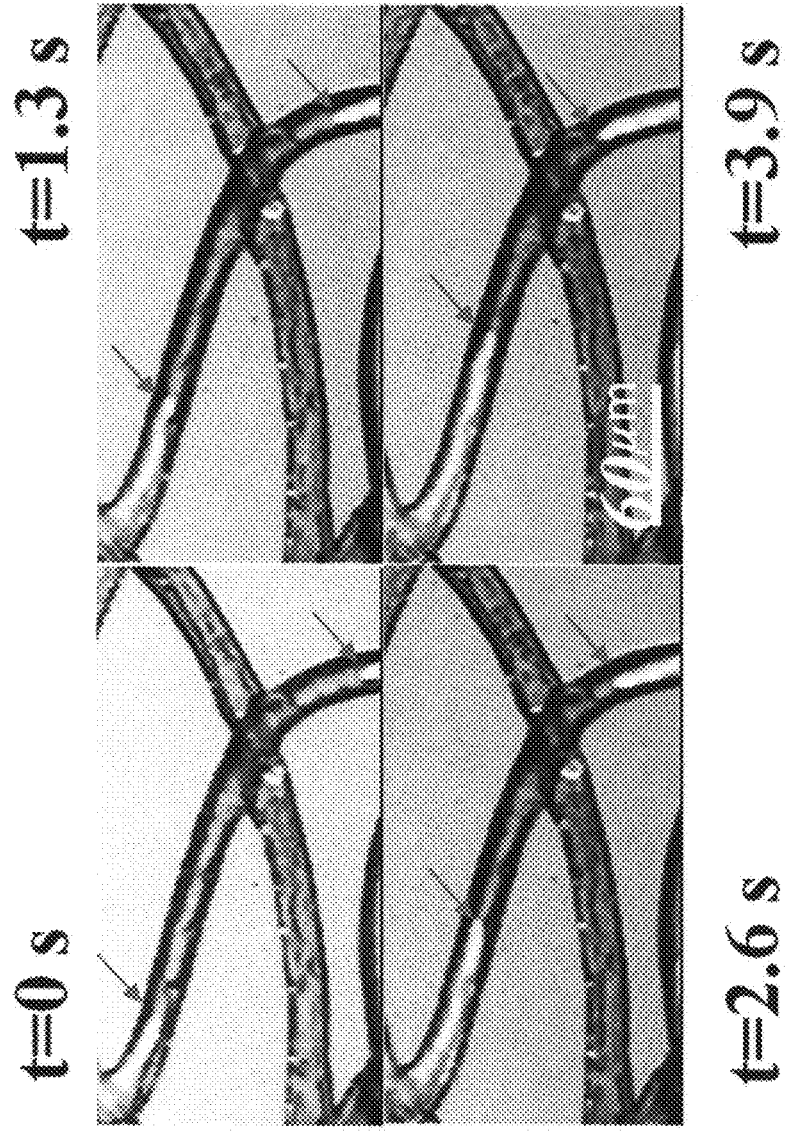
Figure 9I:
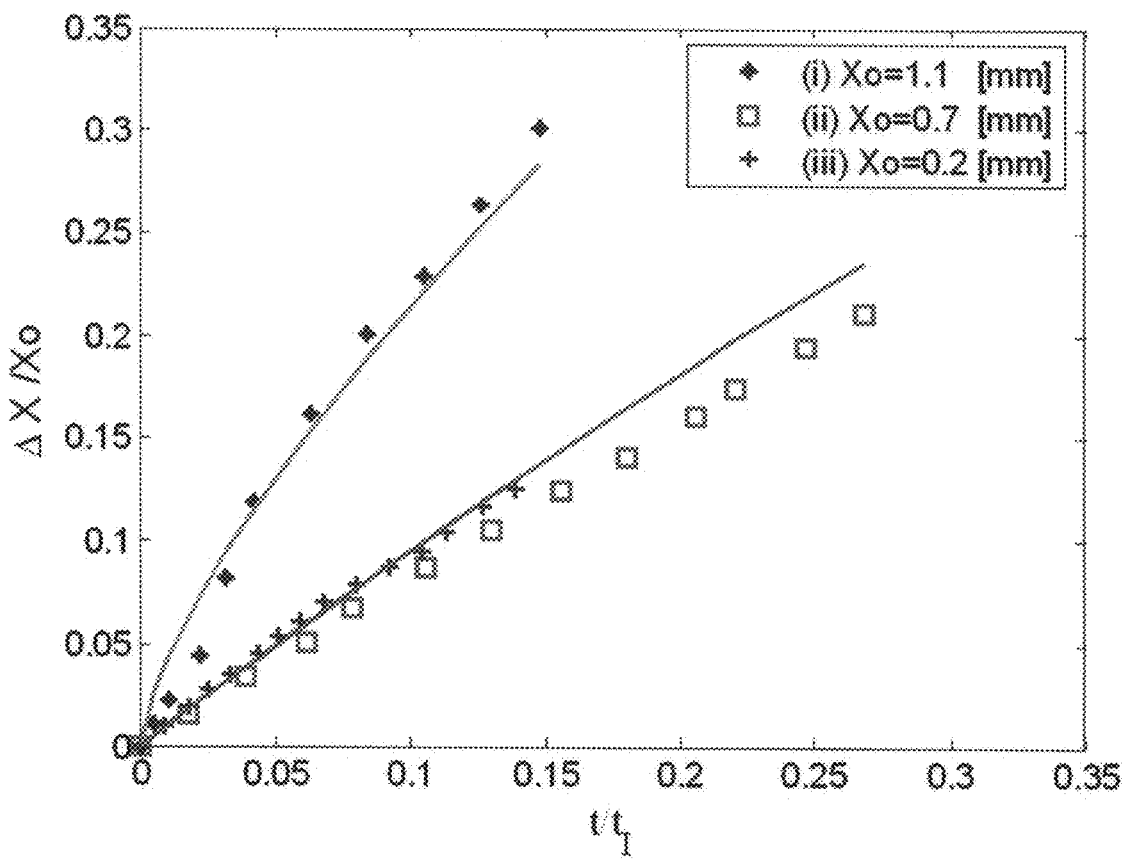

FIG. 8 is a schematic illustration of the core solvent evaporation process from the co-electrospun fiber, FIGS. 9a-i depict the evaporation process of PCL/PEO (shell 1, core 1) microtubes. FIGS. 9a-d—Images taken at 2 seconds intervals [t=0 seconds (FIG. 9a), t=2 seconds (FIG. 9b), t=4 seconds (FIG. 9c) and t=6 seconds (FIG. 9d)] depict the evaporation process of the PCl/PEO microtube with the following diameter and slugs' length: $X_0$=0.7 mm, a=5 µm, b=6 µm, (test ii). The meniscus position is marked by arrows; FIGS. 9e-h—Images taken at t=0 (FIG. 9e), t=1.3 (FIG. 9f), t=2.6 (FIG. 9g) and t=3.9 (FIG. 9h) depict evaporation of the PCL/PEO microtube with the following diameter and slugs' length: $X_0$=0.2 mm, a=7 µm, b=8 µm, (test iii), the distance from the center of the slug to the outlet was L=0.22 mm. The meniscus position is marked by arrows; FIG. 9i—a graph depicting the displacement (measured in mm) of the meniscus (presented as Δx/x0) as function of time, experimental (dots) and calculated (solid line) results where tests i and ii were calculated according to Equation (2) and test iii was calculated according to linear combination of Equations (2) and (3). Test iii refers to $X_0$=1.1 mm, a=5 μm, b=6 μm. The relative humidity in these experiments was 40% (H=0.4), and $\Delta X=X_0-X$; The core and shell polymers are described in Table 2 of the Examples section which follows.

Figure 10A:
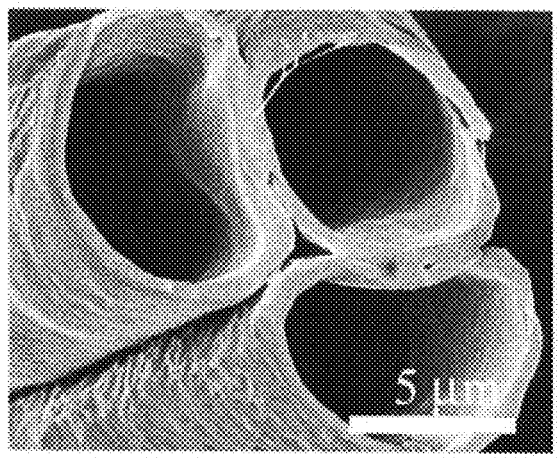
Figure 10B:
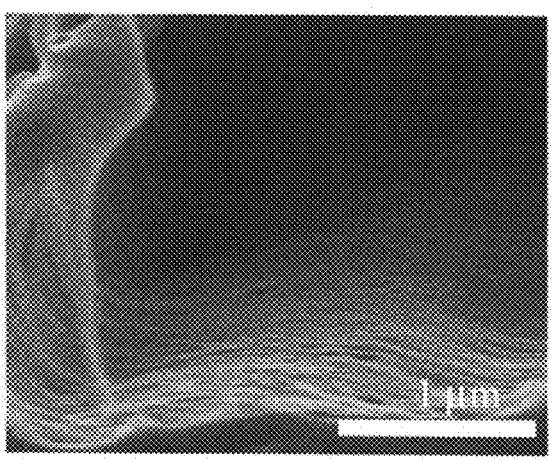

FIGS. 10a-b are HRSEM micrographs of the inner pattern of PCL/PEO microtubes (shell 1, core 1). The core and shell polymers are described in Table 2 of the Examples section which follows.

Figures 11A, 11B, 11C, 11D:
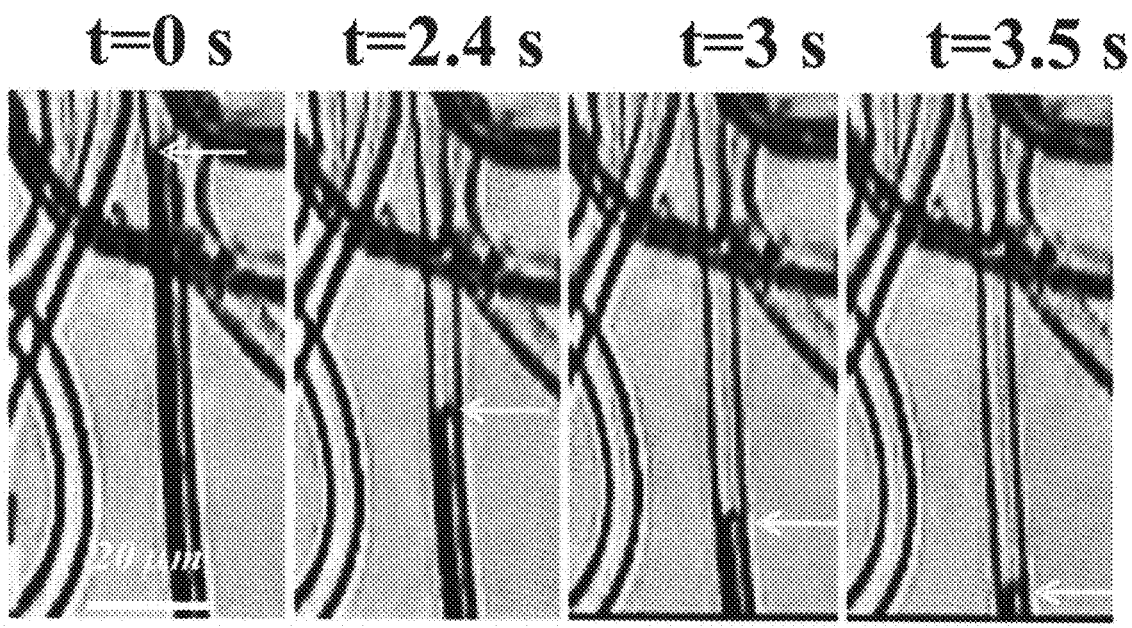
Figure 11E:
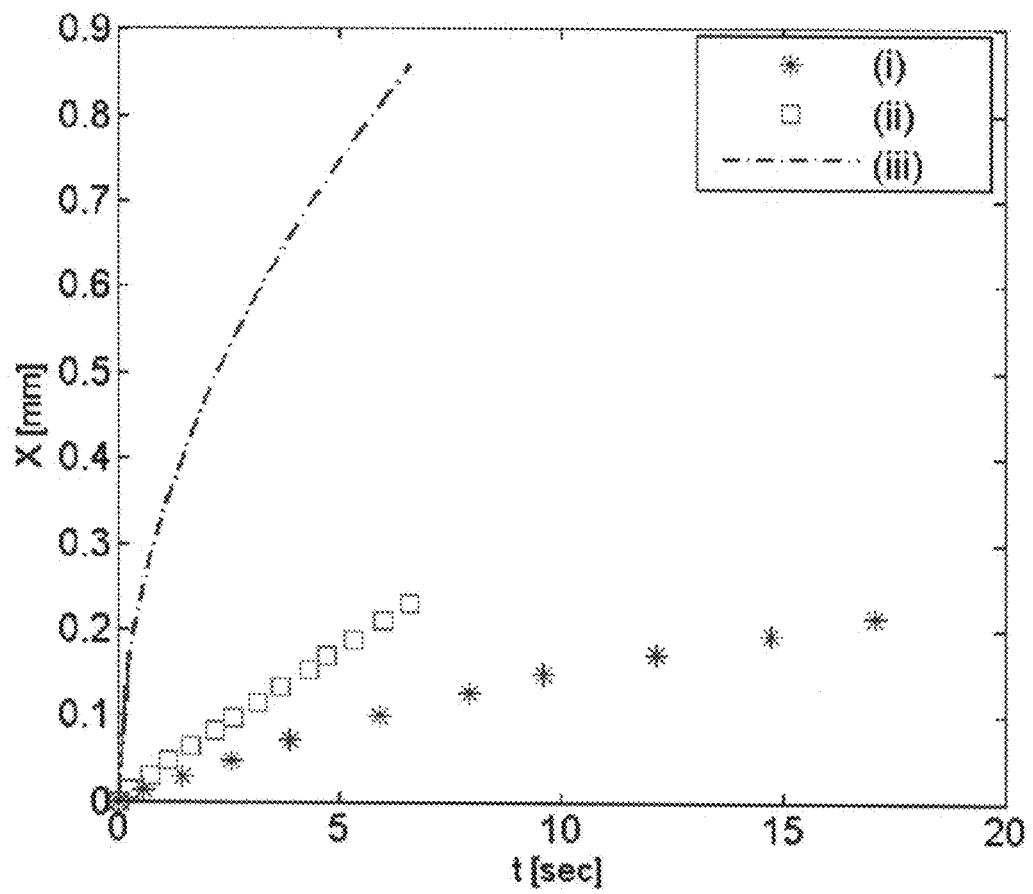

FIGS. 11a-e depict silicon oil capillary filling of microtubes. FIGS. 11a-d—Sequence of video frames of silicon oil capillary filling of micro-tubes PCL/PEO (shell 1, core 1) taken at t=0 seconds (FIG. 11a), t=2.4 (FIG. 11b), t=3 (FIG. 11c) and t=3.5 (FIG. 11d). The meniscus position is marked by arrows; FIG. 11e—a graph depicting the displacement of the meniscus as function of time of two experiments (i, ii) with micro-tubes (shell 1, core 1), and (iii) Washburn capillary rise model $\vec{x} \cong 0.31\sqrt{t}$.
The core and shell polymers are described in Table 2 of the Examples section which follows.

Figure 12A:
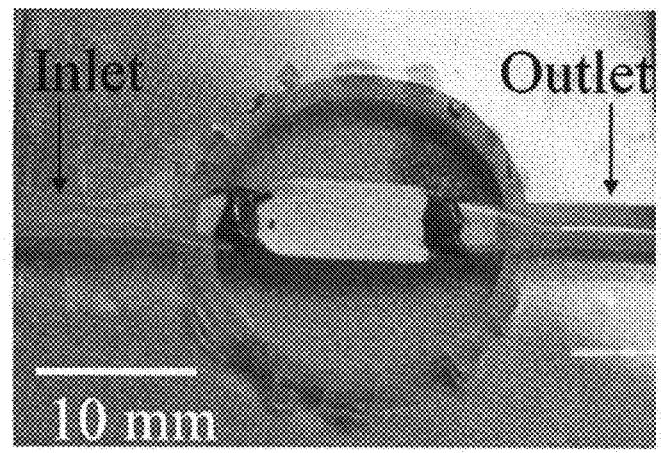
Figure 12B:
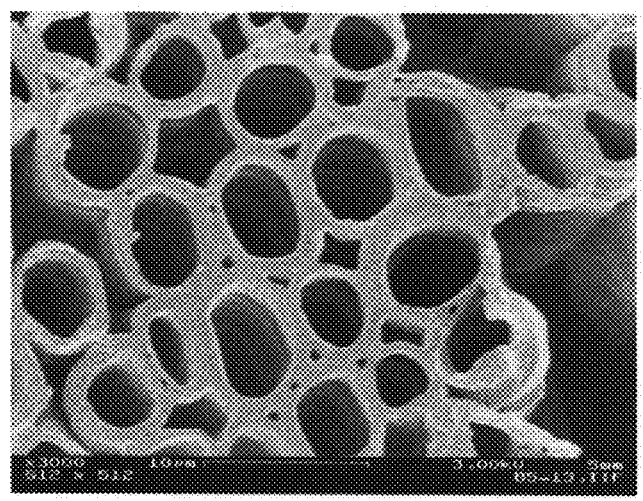

FIGS. 12a-b depict a microfluid construct. FIG. 12a—An optical image of the vascular microfluidic network connected with Teflon micro tubing. Shown are the inlet and outlets of the microfluidic network. The construct is mounted on a sheet of plastic for handling purposes; FIG. 12b—Scanning electron microscope image of the cross-section of the micro fluidic.

Figure 13:
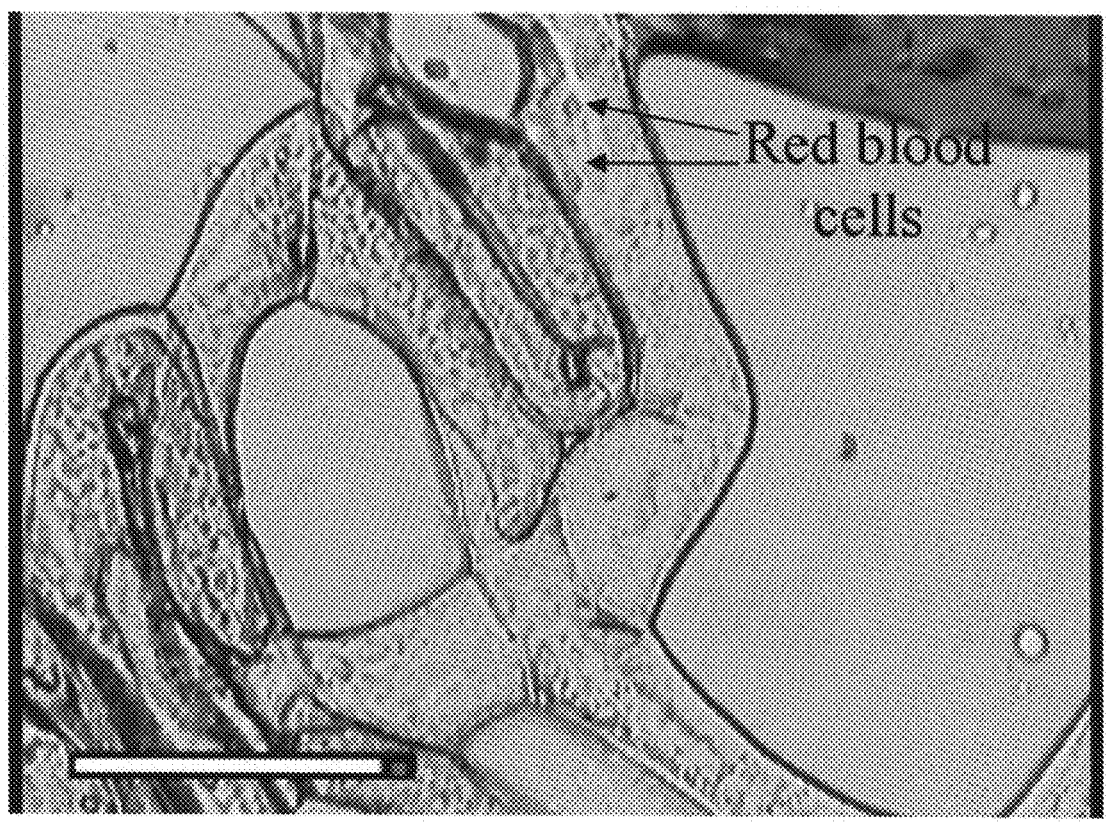

FIG. 13 is an optical still image, depicting top view of the vascular microfluidic network, showing individual blood red cells. Size bar=40 micro-meter.

DESCRIPTION OF EMBODIMENTS OF THE INVENTION

Some embodiments of the present invention provide microtubes and methods of producing same. More specifically, microtubes of the present invention are formed by electrospinning.

The principles and operation of the method of producing a microtube according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of the chemical and physics art.

While reducing some embodiments of the invention to practice, the present inventors uncovered a one-step procedure for producing microtubes.

As is shown in FIGS. 1, 2a-d, 3a-b, 10a-b, and described in Examples 1-8 of the Examples section which follows, the present inventors were able to produce hollow polymeric fibers i.e., microtubes, by electrospinning through co-axial capillaries two polymeric solutions carefully selected to produce microtubes characterized by a strong microtube shell of an even width (of about 100 nm to about 20 micrometer) which does not collapse and an internal diameter of about 200 nm to about 50 micrometer. In addition, as shown in FIGS. 7a-b and described in Example 4 of the Examples section which follows, the presence and size of pores in the microtube shell can be easily controlled by the selection of solvents of the shell polymeric solution and/or the inclusion of water-soluble polymers such as PEG. Moreover, the thickness of the microtube shell and the tube diameter can be controlled by the relative flow rate of the shell or coat polymeric solutions (FIGS. 6a-c, Example 3 of the Examples section which follows). Thus, a pair of biocompatible and biodegradable polymers (e.g., PEO as a coat polymer and PCL as shell polymer, Table 2, hereinbelow) was used to form bio-microtubes. As is further described in Examples 6 and 8 of the Examples section which follows, these microtubes can be filled with various liquids such as silicon oil (See FIG. 11a-e) or blood (FIGS. 12a-b and 13) which are capable of flowing therein, demonstrating the possible usage of these tubes as microfluidics.

Thus, according to one aspect of the invention there is provided a method of producing a microtube. The method is effected by co-electrospinning two polymeric solutions through co-axial capillaries to thereby produce the microtube, wherein a first polymeric solution of the two polymeric solutions is for forming a shell of the microtube and a second polymeric solution of the two polymeric solutions is for forming a coat over an internal surface of the shell, the first polymeric solution is selected solidifying faster than the second polymeric solution and a solvent of the second polymeric solution is selected incapable of dissolving the first polymeric solution.

As used herein the term "microtube" refers to a hollow tube having an inner diameter of e.g., about 200 nm to about 50 μm and an outer diameter of e.g., about 0.5 μm to 100 μm.

As used herein the phrase "co-electrospinning" refers to a process in which at least two polymeric solutions are electrospun from co-axial capillaries (i.e., at least two capillary dispensers wherein one capillary is placed within the other capillary while sharing a co-axial orientation) forming the spinneret within an electrostatic field in a direction of a collector. The capillary can be, for example, a syringe with a metal needle or a bath provided with one or more capillary apertures from which the polymeric solution can be extruded, e.g., under the action of hydrostatic pressure, mechanical pressure, air pressure and high voltage.

The collector serves for collecting the electrospun element (e.g., the electrospun microtube) thereupon. Such a collector can be a rotating collector or a static (non rotating) collector. When a rotating collector is used, such a collector may have a cylindrical shape (e.g., a drum), however, it will be appreciated that the rotating collector can be also of a planar geometry (e.g., an horizontal disk). The spinneret is typically connected to a source of high voltage, preferably of positive polarity, while the collector is grounded, thus forming an electrostatic field between the dispensing capillary (dispenser) and the collector. Alternatively, the spinneret can be grounded while the collector is connected to a source of high voltage, preferably with negative polarity. As will be appreciated by one ordinarily skilled in the art, any of the above configurations establishes motion of positively charged jet from the spinneret to the collector. Reverse polarity for establishing motions of a negatively charged jet from the spinneret to the collector are also contemplated.

At a critical voltage, the charge repulsion begins to overcome the surface tension of the liquid drop. The charged jets depart from the spinneret and travel within the electrostatic field towards the collector. Moving with high velocity in the inter-electrode space, the jet stretches and solvent therein evaporates, thus forming fibers which are collected on the collector.

As mentioned above, microtubes of some embodiments of the present invention are formed by electrospinning. Thus, the first polymeric solution is injected into the outer capillary of the co-axial capillaries while the second polymeric solution is injected into the inner capillary of the co-axial capillaries. In order to form a microtube (i.e., a hollow structure, as mentioned above), the first polymeric solution (which is for forming a shell of the microtube) solidifies faster than the second polymeric solution (also referred herein as a core polymeric solution, and is for forming a coat over an internal surface of the shell). In addition, the formation of a microtube also requires that the solvent of the second polymeric solution is incapable of dissolving the first polymeric solution.

Thus, the solidification rates of the first and second polymeric solutions are critical for forming the microtube. For example, for a microtube of about 100 μm, the solidification of the first polymer (of the first polymeric solution) can be within about 30 milliseconds (ms) while the solidification of the second polymer (of the second polymeric solution) can be within about 10-20 seconds. It will be appreciated that solidification may be a result of polymerization rate and/or evaporation rate.

According to an embodiment of the invention, the solvent of the first polymeric solution evaporates faster than the solvent of second polymeric solution (e.g., the solvent of the first polymeric solution exhibits a higher vapor pressure than the solvent of the second polymeric solution).

According to an embodiment of the invention, the rate of evaporation of the solvent of the first polymeric solution is at least about 10 times faster than that of the solvent of second polymeric solution. Thus, the evaporation rate of the solvent of the first polymeric solution can be at least about 100 times faster or at least about 1000 times faster than the evaporation rate of the solvent of second polymeric solution. For example, the evaporation of chloroform is significantly faster than the evaporation of an aqueous solution (water) due to the high vapor pressure at room temperature of the chloroform (195 mmHg) vs. that of the aqueous solution (23.8 mmHg).

It will be appreciated that by selecting a solvent of the second polymeric solution which is incapable of dissolving the first polymeric solution, the polymer of the first polymeric solution can solidify and form a strong microtube shell which does not collapse, and is characterized by an even width. Thus, the first polymeric solution (e.g., the solvent of the first polymer) is substantially immiscible in the solvent of the second polymer.

As used herein the phrase "polymeric solution" refers to a soluble polymer, i.e., a liquid medium containing one or more polymers, co-polymers or blends of polymers dissolved in a solvent. The polymer used by the invention can be a natural, synthetic, biocompatible and/or biodegradable polymer.

The phrase "synthetic polymer" refers to polymers that are not found in nature, even if the polymers are made from naturally occurring biomaterials. Examples include, but are not limited to, aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and combinations thereof.

Suitable synthetic polymers for use by the invention can also include biosynthetic polymers based on sequences found in collagen, elastin, thrombin, fibronectin, starches, poly(amino acid), poly(propylene fumarate), gelatin, alginate, pectin, fibrin, oxidized cellulose, chitin, chitosan, tropoelastin, hyaluronic acid, polyethylene, polyethylene terephthalate, poly(tetrafluoroethylene), polycarbonate, polypropylene and poly(vinyl alcohol), ribonucleic acids, deoxyribonucleic acids, polypeptides, proteins, polysaccharides, polynucleotides and combinations thereof.

The phrase "natural polymer" refers to polymers that are naturally occurring. Non-limiting examples of such polymers include, silk, collagen-based materials, chitosan, hyaluronic acid, albumin, fibrinogen, and alginate.

As used herein, the phrase "co-polymer" refers to a polymer of at least two chemically distinct monomers. Non-limiting examples of co-polymers include, polylactic acid (PLA)-polyethyleneglycol (PEG), polyethylene glycol terephthalate (PEGT)/polybutylene terephthalate (PBT), PLA-polyglycolic acid (PGA), PEG-polycaprolactone (PCL) and PCL-PLA.

As used herein, the phrase "blends of polymers" refers to the result of mixing two or more polymers together to create a new material with different physical properties.

The phrase "biocompatible polymer" refers to any polymer (synthetic or natural) which when in contact with cells, tissues or body fluid of an organism does not induce adverse effects such as immunological reactions and/or rejections and the like. It will be appreciated that a biocompatible polymer can also be a biodegradable polymer.

According to an embodiment of the invention, the first and the second polymeric solutions are biocompatible.

Non-limiting examples of biocompatible polymers include Polyesters (PE), PCL, Calcium sulfate, PLA, PGA, PEG, polyvinyl alcohol, polyvinyl pyrrolidone, Polytetrafluoroethylene (PTFE, teflon), Polypropylene (PP), Polyvinylchloride (PVC), Polymethylmethacrylate (PMMA), Polyamides, segmented polyurethane, polycarbonate-urethane and thermoplastic polyether urethane, silicone-polyether-urethane, silicone-polycarbonate-urethane Collagen, PEG-DMA, Alginate, Hydroxyapatite and Chitosan, blends and copolymers thereof.

The phrase "biodegradable polymer" refers to a synthetic or natural polymer which can be degraded (i.e., broken down) in the physiological environment such as by proteases. Biodegradability depends on the availability of degradation substrates (i.e., biological materials or portion thereof which are part of the polymer), the presence of biodegrading materials (e.g., microorganisms, enzymes, proteins) and the availability of oxygen (for aerobic organisms, microorganisms or portions thereof), carbon dioxide (for anaerobic organisms, microorganisms or portions thereof) and/or other nutrients. Examples of biodegradable polymers/materials include, but are not limited to, collagen (e.g., Collagen I or IV), fibrin, hyaluronic acid, polylactic acid (PLA), polyglycolic acid (PGA), polycaprolactone (PCL), polydioxanone (PDO), trimethylene carbonate (TMC), polyethyleneglycol (PEG), Collagen, PEG-DMA, Alginate, chitosan copolymers or mixtures thereof.

According to an embodiment, the polymeric solution can be made of one polymer or more, each can be a polymer or a co-polymer such as described hereinabove.

According to an embodiment of the invention, the polymeric solution of the invention is a mixture of at least one biocompatible polymer and a co-polymer (either biodegradable or non-biodegradable).

According to an embodiment of the invention, the electrospun shell can be made of a polymer such as poly (e-caprolactone) (PCL), polyamide, poly(siloxane), poly (silicone), poly(ethylene), poly(vinyl pyrrolidone), poly(2-hydroxy ethylmethacrylate), poly(N-vinyl pyrrolidone), poly(methyl methacrylate), poly(vinyl alcohol), poly(acrylic acid), poly(vinyl acetate), polyacrylamide, poly(ethylene-co-vinyl acetate), poly(ethylene glycol), poly(methacrylic acid), polylactide, polyglycolide, poly(lactide-coglycolide), polyanhydride, polyorthoester, poly(carbonate), poly(acrylo nitrile), poly(ethylene oxide), polyaniline, polyvinyl carbazole, polystyrene, poly(vinyl phenol), polyhydroxyacid, poly(caprolactone), polyanhydride, polyhydroxyalkanoate, polyurethane, collagen, albumin, alginate, chitosan, starch, hyaluronic acid, and blends and copolymers thereof.

According to an embodiment of the invention, the electrospun coat can be made of a polymer such as poly(acrylic acid), poly(vinyl acetate), polyacrylamide, poly(ethylene-co-vinyl acetate), poly(ethylene glycol), poly(methacrylic acid), polylactide polyglycolide, poly(lactide-coglycolide), polyanhydride, polyorthoester, poly(carbonate), poly(ethylene oxide), polyaniline, polyvinyl carbazole, polystyrene, poly(vinyl phenol), polyhydroxyacid, alginate, starch, hyaluronic acid, and blends and copolymers thereof.

It will be appreciated that in order to form a hollow microtube, the solvent of the second polymeric solution may evaporate while the polymer forms a thin layer on the internal surface of the shell.

According to an embodiment of the invention, the solvent of the second polymeric solution is capable of evaporating through the internal surface of the shell.

In addition, it will be appreciated that during the formation of the microtube shell (i.e., the solidification of the first polymeric solution) the second polymeric solution flows within the internal surface of the shell.

According to an embodiment of the invention, the second polymeric solution is selected capable of wetting the internal surface of the shell.

Various polymeric solutions which are known in the art as capable of wetting other polymeric surfaces (forming the shell) can be used. Following is a non-limiting list of pairs of polymeric solutions in which the second polymeric solution is capable of wetting the internal surface of the shell formed by the first polymeric solution.

TABLE 1

Pairs of polymeric solutions for producing the microtube of the invention

| First polymeric solution forming the shell | Second polymeric solution capable of wetting the internal surface of the shell |
|---|---|
| 10% poly (e-caprolactone) (PCL) in chloroform (CHCl$_3$) and 20 dimethylforamide (DMF) (80:20 by weight %) | 4% poly(ethylene oxide) (PEO) in water (H$_2$O) and ethanol (60:40 by weight) |
| Nylon 6,6 in formic acid 7 to 12 wt % | 4% poly(ethylene oxide) (PEO) in water (H$_2$O) and ethanol (60:40 by weight) |
| Poly(L-lactide-co-glycolide) (PLGA 10:90) in hexafluroisopropanol (HFIP) concentrations ranging from 2 to 7 weight % solution. | 4% poly(ethylene oxide) (PEO) in water (H$_2$O) and ethanol (60:40 by weight) |
| Poly(L-lactide-co-glycolide) (PLGA 15:85) hexafluroisopropanol (HFIP) concentrations ranging from 2 to 7 weight % solution. | 4% poly(ethylene oxide) (PEO) in water (H$_2$O) and ethanol (60:40 by weight) |
| poly(lactide-co-glycolide) (PLGA; l-lactide/glycolide__50/50) 1,1,1,3,3,3-hexafluoro-2-propanol (HFIP) concentrations ranging from 2 to 7 weight % solution. | 4% poly(ethylene oxide) (PEO) in water (H$_2$O) and ethanol (60:40 by weight) |
| polyglycolide (PGA) in chloroform 3-10 weight % solution. | 9% poly(vinyl alcohol) (PVA) in water and ethanol (50:50 by weight) |
| poly(l-lactide) (PLA) in chloroform 3-10 weight % solution. | 9% poly(vinyl alcohol) (PVA) in water and ethanol (50:50 by weight) |
| Segmented polyurethane in DMF and THF (80:20 by weight %) | 9% poly(vinyl alcohol) (PVA) in water and ethanol (50:50 by weight) |
| Polyurethane in DMF and tetrahydrofuran, THF (80:20 by weight %) | 9% poly(vinyl alcohol) (PVA) in water and ethanol (50:50 by weight) |

TABLE 1-continued

Pairs of polymeric solutions for producing the microtube of the invention

| First polymeric solution forming the shell | Second polymeric solution capable of wetting the internal surface of the shell |
| --- | --- |
| PLGA (poly lactic-co-glycolic acid) in chloroform and DMSO (dimethyl sulfoxide) in chloroform and DMSO (80:20 by weight %). | 9% poly(vinyl alcohol) (PVA) in water and ethanol (50:50 by weight) |
| 10% PCL in CHCl$_3$/DMF (80:20 by weight) | 6% PEO in H$_2$O/EtOH (60:40 by weight) |
| 9% PCL in CHCl$_3$/DMSO (90:10 by weight) | 7% PEO in H$_2$O |
| 10% PCL in CHCl$_3$/DMF (80:20 by weight) | 9% PVA in ethanol/water (50:50 by weight) |

According to an embodiment of the invention, the first and the second polymeric solutions are selected from the group of: 10% poly (e-caprolactone) (PCL) in chloroform (CHCl$_3$) and 20 dimethylforamide (DMF) (80:20 by weight) as the first polymeric solution and 4% poly(ethylene oxide) (PEO) in water (H$_2$O) and ethanol (60:40 by weight) as the second polymeric solution, 10% PCL in CHCl$_3$ and DMF (80:20 by weight) as the first polymeric solution and 6% PEO in H$_2$O and ethanol (60:40 by weight) as the second polymeric solution, 9% PCL in CHCl$_3$ and DMF (90:10 by weight) as the first polymeric solution and 7% PEO in H$_2$O as the second polymeric solution, and 10% PCL in CHCl$_3$ and DMF (800:20 by weight) as the first polymeric solution and 9% poly(vinyl alcohol) (PVA) in water and ethanol (50:50 by weight) as the second polymeric solution.

As described in Example 3 of the Examples section which follows, the thickness and internal diameter of the microtube can be controlled during the electrospinning process. For example, the ratio between the flow rates of the first and second polymeric solutions can determine the fiber outer diameter and whether the resulting fiber is hollow or solid (see also FIGS. 6a-c).

According to an embodiment of the invention the thickness of the microtube shell of the invention can vary from a few nanometers to several micrometers, such as from 100 nm to 20 µm, e.g., from 200 nm to 10 µm, from 100 nm to 5 µm, from 100 nm to 1 µm, e.g., about 500 nm.

According to an embodiment of the invention the internal diameter of the microtube shell of the invention can vary from a few nanometers to several micrometers, such as from 50 nm to 50 µm, e.g., from 100 nm to 20 µm, from 200 nm to 10 µm, from 500 nm to 5 µm, from 1 µm to 5 µm, e.g., about 3 µm.

It will be appreciated that the microtube shell can be extensively porous thus creating a "breathing" tube, or on the other hand can be totally sealed thus forming a one-axial flow system. A "breathing" microtube, i.e., a microtube which comprises pores in the shell thereof, can be formed by including a high percent of a volatile component in the first polymeric solution forming the shell. For example, a high percentage of chloroform (e.g., at least 80%) within the polymeric solution can result in a porous shell (see for example, FIG. 7a and Example 4 of the Examples section which follows).

According to an embodiment of the invention, in order to form a porous shell the first polymeric solution includes a volatile solvent such as Tetrahydrofuran (THF), Chloroform, acetone, or trifluoroethanol (TFE).

Additionally or alternatively, the pores in the shell of the microtube of the invention can be formed by including a water-soluble polymer such as polyethylene glycol (PEG) in the first polymeric solution. Thus, following wetting of the microtube in a water-based solution, the water-soluble polymer is dissolved and pores are formed. For example, the first polymeric solution may include a blend of polymers in which one is water-soluble and the other is water-insoluble. For example, as is shown in FIG. 7b and described in Example 4 of the Examples section which follows, a blend of PEG and PCL was used as a first polymeric solution for forming a porous shell.

According to an embodiment of the invention, the first polymeric solution comprises PEG for poring the shell. For example, to generate pores of >150 nm diameter, the first polymeric solution may include about 4% PEG Mw 35 kDa Similarly, to generate pores of <150 nm diameter, the first polymeric solution may include about 2% Mw PEG 6 kDa.

It will be appreciated that the pores in the electrospun shell can be also generated after completion of the electrospinning process by passing an electrical spark through the electrospun shell, essentially as described in PCT WO 2006/106506 to the present inventors. Such an electrical spark can be generated by any electrical spark producing element, such as, but not limited to, a needle-like electrode. The electrical spark can vary depending on the applied voltage, its duration and the distance between the electrode and the electrospun shell.

The electrical spark is produced with an electric field which is sufficient to generate air breakdown. At normal conditions, such breakdown occurs at about 30 kV/cm. The electric field can be generated by a potential difference of at least 10 kV, e.g., at least 15 kV. Thus, the breakdown field is generated by positioning the electrode at a distance of about 10 mm, e.g., at a distance of 5 mm or 1 mm from the electrospun shell. The voltage used to generate the electrical spark can be provided for a time period of about 5 seconds, e.g., about 1 second, or 0.1 second Additionally or alternatively, it will be appreciated that the pores in the electrospun shell can be also generated by passing a heated puncturing element through the electrospun shell.

As used herein, the phrase "puncturing element" refers to any sharp and pointed element, e.g., a metal implement which is capable of being heated and thus puncturing (i.e., making a hole) the electrospun element. Non-limiting examples of such puncturing elements include, a metal needle and a metal pin.

Thus, the puncturing element is heated to a temperature of at least 90° C., e.g., at least 91° C., 92° C., 93° C., 94° C., 95° C., 96° C., 97° C., 98° C., 99° C., 100° C., say about 100° C., about 101° C., about 102° C. and the passing of the puncturing element through the electrospun shell can be effected for a time period of 0.1-10 seconds, e.g., for a time period of 1-5 seconds.

Additionally or alternatively, it will be appreciated that the pores in the electrospun shell can be also generated by a pulsed or continuous laser beam. The laser beam can be generated by any laser device capable of providing laser radiation which ablate or melt the polymer fibers to some extent. These include, but are not limited to, the following laser devices: Excimer laser device, Kr based laser device, Xe based laser device, Er based laser device, Ho:YAG laser device, carbon-dioxide laser device, Nd based laser device and laser diode device. Kr based laser devices include, but are not limited to krypton-fluoride (KrF) laser devices. Xe based laser devices include, but are not limited to xenon-fluoride (XeF) laser devices. Er based laser devices include, but are not limited to, Er:YAG, Er:YSGG, Er:glass and the like. Nd based laser devices include, but are not limited to, Nd:YAG, Nd:YLF, Nd:glass and the like. Also contemplated are $CO_2$ and Dye laser devices.

For example, perforation of an electrospun shell is performed using a pulsed laser beam at a specific energy (e.g., 200 Watt) which is provided at a specific rate (e.g., 200 Hz), using several pulses for each hole.

It will be appreciated that in order to enable flow of a liquid within the microtube, i.e., along the coat polymer covering the internal surface of the shell, the surface (thin film) formed by the coat polymer should be designed such that it can be wetted by the liquid-of-interest. The wettability of polymer films by liquids are known in the art. For example, silicone oil or water can wet a surface made of a PEO polymer. It will be appreciated that the wettability of the coat polymer covering the internal surface of the shell can be controlled (e.g., improved) for example by attaching functional groups such as hydroxyl group (OH) which increase the hydrophilicity of the coat by a plasma treatment [see Thurston R M, Clay J D, Schulte M D, Effect of atmospheric plasma treatment on polymer surface energy and adhesion, Journal of Plastic Film & Sheeting 23 (1): 63-78 January 2007; which is incorporated within by reference].

Thus, the present invention provides a microtube which comprises an electrospun shell and an electrospun coat over an internal surface of the shell.

As used herein, the phrase "electrospun shell" refers to a hollow element of a tubular shape, made of one or more polymers, produced by the process of electrospinning as detailed above.

As used herein the phrase "electrospun coat" refers to a thin layer covering the internal surface of the shell of the microtube of the invention which is made of one or more polymers by the process of electrospinning as detailed above.

One of ordinary skill in the art will know how to distinguish an electrospun object from objects made by means which do not comprise electrospinning by the high orientation of the macromolecules, the skin (e.g., shell) morphology, and the typical dimensions of the microtube which are unique to electrospinning.

It will be appreciated that the microtube produced by the method of the invention can form an individual (e.g., single or separated) microtube or can form part of a plurality (e.g., an aligned array) of microtubes which can be either connected to each other or separated (as single, not-connected microtubes).

Thus, for the production of a single microtube a fork like clip is attached to the edge of the rotating disk. The disk is rotating for 1-2 seconds and individual microtubes are collected between the fork tooth. In a similar way individual electrospun fibers were collected (see E. Zussman, M. Burman, A. L. Yarin, R. Khalfin, Y. Cohen, "Tensile Deformation of Electrospun Nylon 6,6 Nanofibers," *Journal of Polymer Science Part B: Polymer Physics,* 44, 1482-1489, 2006, herein incorporated by reference in its entirety).

Alternatively, when using a rotating collector, a plurality of microtubes can be formed and collected on the edge of the collector as described elsewhere for electrospun fibers (A. Theron, E. Zussman, A. L. Yarin, "Electrostatic field-assisted alignment of electrospun nanofibers", *Nanotechnology J.,* 12, 3: 384-390, 2001; herein incorporated by reference in its entirety).

The plurality of microtubes can be arranged on a single layer, but, more preferably, the plurality of microtubes define a plurality of layers hence form a three dimensional structure. The microtubes can have a general random orientation, or a preferred orientation, as desired e.g., when the fibers are collected on a cylindrical collector such as a drum, the microtubes can be aligned predominantly axially or predominantly circumferentially. Different layers of the electrospun microtubes can have different orientation characteristics. For example, without limiting the scope of the present invention to any specific ordering or number of layers, the microtubes of a first layer can have a first predominant orientation, the microtubes of a second layer can have a second predominant orientation, and the microtubes of third layer can have general random orientation.

According to an embodiment of the invention a liquid fills the microtube. The liquid may be blood or blood components, e.g., plasma, red blood cells, coagulation factors, white blood cells, leukocytes, neutrophils, or any physiological solution which includes water and physiological concentrations of salts (e.g., phosphate buffered saline) and/or proteins.

It will be appreciated that the microtube of the invention may be configured as or in a microfluidics device. "Lab-on-a-chip" are described in a series of review articles [see for example, Craighead, H. Future lab-on-a-chip technologies for interrogating individual molecules. Nature 442, 387-393 (2006); deMello, A. J. Control and detection of chemical reactions in microfluidic systems. Nature 442, 394-402 (2006); El-Ali, J., Sorger, P. K. & Jensen, K. F. Cells on chips. Nature 442, 403-411 (2006); Janasek, D., Franzke, J. & Manz, A. Scaling and the design of miniaturized chemical-analysis systems. Nature 442, 374-380 (2006); Psaltis, D., Quake, S. R. & Yang, C. H. Developing optofluidic technology through the fusion of microfluidics and optics. Nature 442, 381-386 (2006); Whitesides, G. M. The origins and the future of microfluidics. Nature 442, 368-373 (2006); Yager, P. et al. Microfluidic diagnostic technologies for global public health. Nature 442, 412-418 (2006)] each of which is fully incorporated herein by reference].

Thus, the microtube of the invention (or a microfluidic device comprising same) can be used as a graft of the desired length, width and internal diameter to replace a damaged, injured or diseased blood vessel (e.g., in a coronary artery bypass graft (CABG) surgery, or for treating other atherosclerosis or ischemic diseases).

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Current Protocols in Immunology" Volumes I-Ill Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); D. H. Reneker, A. Yarin, E. Zussman, S. Koombhongse, and W. Kataphinan, "Nanofiber Manufacturing: Toward Better Process Control", in: Polymeric Nanofibers, ACS Symposium Series, Vol. 918, Ed. Reneker, D. H.; Fong, H., ACS, Washington D.C., 2005; A. L. Yarin, E. Zussman, A. Greiner, J. H. Wendorff, "Material encapsulation and transport in core-shell micro/nanofibers, polymer and carbon nanotubes and micro/nano channels", J. of Materials Chemistry, 17, 2585-2599, 2007; A. Greiner, J. H. Wendorff, A. L. Yarin, E. Zussman, "Biohybrid nanosystems with polymer nanofibers and nanotubes," Applied Microbiology and Biotechnology, 71, 387-393, 2006; D. H. Reneker, A. L. Yarin, E. Zussman, H. Xu, "Electrospinning of nanofibers from polymer solutions," Advances in Applied Mechanics (Review Paper), 41, 43-195, 2007; Z. M. Huang, Y. Z. Zhang, M. Kotaki, S. Ramakrishna (2003) Composites Science and Technology 63:2223; S. Ramakrishna, K. Fujihara, W.-e. Teo, Lim, T. C., Z. Ma, An Introduction to Electrospinning and Nanofibers, World Scientific Publishing Company, 2005; all of which are incorporated by reference as if fully set forth herein. Other general references are provided throughout this document. The procedures therein are believed to be well known in the art and are provided for the convenience of the reader. All the information contained therein is incorporated herein by reference.

GENERAL MATERIALS AND EXPERIMENTAL METHODS

Polymer Solutions and Characterization—

The polymers, poly (e-caprolactone) (PCL) $M_n$ 80 kDa, poly(ethylene oxide) (PEO) $M_w$ 600 kDa, poly(vinyl alcohol) (PVA) $M_w$ 100 kDa and polyethylene glycol (PEG) Mn 6 kDa were purchased from Sigma-Aldrich and used without further treatment or purification. The solvents, chloroform, dimethylforamide (DMF), ethanol and the phosphate buffer saline (PBS-Dulbecco's) were also purchased from Sigma-Aldrich. Deionized water was used for the aqueous solution. The compositions of the core and shell polymeric solutions are given in Table 2, hereinbelow.

TABLE 2

Core and shell polymers used to produce electrospun microtubes

| | Polymer | Solvent | Polymer content % (w/w) | Conductivity (mS cm$^{-1}$) | Shear Viscosity (cP) |
|---|---|---|---|---|---|
| Shell 1 | PCL $M_n$ = 80 KDa | Chloroform/DMF 80/20 (by weight) | 10 | 1 | 1300 |
| Shell 2 | PCL $M_n$ = 80 KDa | Chloroform/DMF 90/10 (by weight) | 10 | / | / |
| Shell 3 | PCL:PEG $M_n$ (PCL) = 80 KDa $M_n$ (PEG) = 6 KDa | Chloroform/DMF 80/20 (by weight) | 9:2 | / | / |
| Core 1 | PEO $M_w$ = 600 KDa | Ethanol/water 40/60 (by weight) | 4 | 11-13 | 2700 |
| Core 2 | PVA Mw = 100 KDa | Ethanol/water 50/50 (by weight) | 9 | 22 | 2000 |
| Core 3 | PEO $M_w$ = 600 KDa | DMF | 4 | 3.2 | 1400 |

TABLE 2-continued

Core and shell polymers used to produce electrospun microtubes

| | Polymer | Solvent | Polymer content % (w/w) | Conductivity (mS cm$^{-1}$) | Shear Viscosity (cP) |
|---|---|---|---|---|---|
| Core 4 | PEO $M_w$ = 600 KDa | Ethanol/water 40/60 (by weight) 1 ml PEO solution + 50 ml PBS | 4 | 200 | 2700 |

Shear viscosities of the solutions were measured at different shear rates using a Couette viscometer (Brookfield DVII programmable viscometer). The reported values are the results of extrapolation to zero shear rates. Conductivity was measured with an Oyster conductivity/temperature meter. The wetting angle of the fluids was measured with a home-made apparatus.

Electrospinning—

Core-shell fibers were fabricated by a co-electrospinning process using the set up described by Sun et al. (Z. Sun, E. Zussman, A. L. Yarin, J. H. Wendorff, A. Greiner, Adv. Mater. 2003, 15, 1929) and Zussman et al. (E. Zussman, A. L. Yarin, V. Bazilevsky, R. Avrahami, M. Feldman, Adv. Mater. 2006, 18, 348). All experiments were conducted at room temperature and relative humidity of 50-60%. For most of the runs the spinning parameters were as follow: electrostatic field of about 0.5 kV/cm, distance between the spinneret and the collector plate between 16 and 20 cm. The flow rates of both the core and shell solutions were controlled by two syringe pumps and are given at each figure caption.

Imaging—

Images of the fibers were obtained using Leo Gemini high resolution scanning electron microscope (HRSEM) at acceleration voltage of 2-4 kV and sample to detector distance of 2-5 mm. The specimens were coated with a thin gold film to increase their conductivity.

For imaging of the fibers' cross-section, the fibers were collected on a rotating wheel following Theron et al.'s approach (A. Theron, E. Zussman, A. L. Yarin, Nanotechnology 2001, 12, 384) and the oriented mat was cut by a special blade using liquid nitrogen. The fibers were imaged by using a light microscope Olympus BX51 (LM) and a digital camera Olympus DP12 with a resolution of 3.34 million pixels.

Example 1

Formation of Microtubes Using One-Step Co-Electrospinning

Experimental Results

Generation of a Microtube Using the Core-Shell Set Up for Electrospinning (Core 1: PEO, Shell 1: PCL, See Table 2, Hereinabove)—

Using the core-shell set-up, a stable compound drop, Taylor cone and subsequent jet were achieved as presented in FIG. 1. A well defined boundary between the core solution and the shell solution in the drop can be seen. In the present case the aqueous PEO solution of the core and the organic solution of PCL in the shell are immiscible and a core-shell nanofiber with a clear boundary between the core and the shell is achieved. It should be mentioned that in this case both solutions are spinnable, that is, can be electrospun as individual components. This is probably partially responsible for the remarkably stable process gained. Indeed, as can be seen by LM micrographs seen in FIG. 2a, a core-shell nanofiber has been achieved with clear separation between the core and the shell and thickness uniformity of both. However, SEM micrographs of the cross-section of these electrospun fibers reveal that the resulting fibers are hollow with a relatively thin and uniform shell and large hollow core as shown in FIG. 2b-d. Thus, the core polymer is coating the inner surface of the shell (formed by the shell polymer). The outer diameter of the tubes is several microns while the thickness of the walls is 0.5-1 μm. A longitudinal section seen in FIG. 2d demonstrates undoubtedly that the hollowness proceeds along the entire fiber. It is then substantiated that the one-step co-electrospinning results in polymeric micro-tubes. It is interesting to note that most of the fibers reserve their cylindrical shape without any catastrophic collapse indicating that the walls, although being relative thin, are sufficiently robust.

A Microtube Formed Using PVA and PCL as Core and Shell Solutions, Respectively—

Similar results were obtained with another system in which the PEO core solution was replaced by a solution of PVA at the concentration given in Table 2 (core 2). The observations given above are valid for this system as well, as can be seen in FIG. 3a-b.

A Microtube Formed Using PEO Dissolved in DMF as a Core and PCL as a Shell—

In FIG. 3c a micrograph of the cross-sections of fibers made of PCL shell and PEO dissolved in DMF (core 3, see Table 2, hereinabove), is presented. It can be seen that micro-tubes are formed as well, however, the thickness of the wall as well as the diameter of the tubes are much less uniform. Also, adjacent tubes tend to merge as can be seen on the right side of the micrograph. Core 2 and core 3 differ in their miscibility with the shell solution. While core 2 is immiscible, core 3 is miscible and the difference between the resulting tubes is clearly seen.

These cases are common in the fact that the shell (shell 1; Table 2, hereinabove) solidifies first due to the relatively volatile solvent from which the shell solution is composed and that the pairs of solutions are immiscible (shell 1, core 1, 2; Table 2, hereinabove). The solidification of the core solution then takes place once the shell is already solid and the overall diameter of the fibers do not change. The solvent evaporation process from the core in the solidified tube is discussed below.

Without being bound by any theory, in order to achieve hollow tubes, the solidification of the shell polymer shall be much faster than the evaporation of the core solvent (the solvent of the coat polymer).

Without being bound by any theory it seems that fast evaporation of the shell solvent and contact with a non-solvent, are responsible for the formation and stabilization of the micro-tubes. Without being bound by any theory the specific process described herein can be considered as a dry/wet electrospinning. The outer surface of the shell experiences a dry spinning process as being exposed to the surrounding air and thus diffusion of the solvent and the evaporation dominate the solidification and the morphology of the outer surface. Since the solvent of the shell solution is rather volatile, the evaporation is fast. On the other hand, the inner layer of the shell experiences a wet spinning process as being in contact with the relatively nonvolatile core solution containing water/ethanol solvent which is a non-solvent to the shell polymer. The core solution then can be regarded as a coagulation bath for the shell. As the aqueous solution starts penetrating the shell an immediate precipitation of the inner layers of the shell takes place. As the affinity between the non-solvent of the core solution and the solvent of the shell solution is good, the precipitation of the polymer due to the inflow of the non-solvent into the shell is very fast (C. C. Pereira, R. Nobrega, C. P. Borges, Beaz. J. Chem. Eng. 2000, 17). Indeed, the affinity between the aqueous solution and DMF is strong while the chloroform tends to separate from the DMF and evaporates first. The formation of a solid "gel filament" at the interface between the core and the shell probably takes place already at the Taylor cone (the residence time of a liquid in the Taylor cone is about 1 sec) (A. L. Yarin, S. Koombhongse, D. H. Reneker, Journal of Applied Physics 2001, 90, 4836). In fact, in such a case which can be generalized to all immiscible solutions co-electrospinning process, the coaxial flow is composed of a solid film enveloping the core solution. This is in contrast to two miscible solutions where the cone and the jet are made of simply two flowing liquids. The overall process encourages a fast solidification of the shell by the two above-mentioned contributions, while the core solution remains wet for a long time after the shell has been solidified.

In the case presented in FIG. 3c the shape of the tubes is relatively poor with a less uniform distinguished shell. Without being bound by any theory, this may be assigned to the fact that the core solvent is DMF (core 3) which is a good solvent to the shell polymer and thus doesn't contribute to fast precipitation of the inner layers of the shell. On the contrary, the DMF facilitates the polymer to remain in solution. Moreover, it is important to emphasize that the electrospinning of the same shell solution only (without core), i.e. an ordinary electrospinning process, didn't result in hollow fibers as can be seen in FIG. 4, although the evaporation process was still fast. Thus, without being bound by any theory, in order to attain hollow tubes both the fast evaporation of the shell solvent and the existence of a slowly solidifying core are required.

Example 2

The Core Polymer Provides Wetting of the Inner Surface of the Shell Polymer

Experimental Results

The Core Polymer (e.g., PEO) Reduces the Surface Tension and Provides the Wetting of the Solidified Shell Polymer (e.g., PCL)—

The polymeric core solution being confined in the solid shell can solidify by either deposition of film onto the inner surface of the tubes or shrinkage to form a solid inner detached fiber. Without being bound by any theory, it appears that the wetting of the inner surface of the shell by the core solution is responsible for the way the core solidifies. In the present case, the PEO which is a surface active polymer (R. Nagarajan, Colloids and Surfaces 1985, 13, 1; D. Suss, Y. Cohen, Y. Talmon, Polymer 1995, 36, 1809), provides a fair wetting of the inner surface of the PCL shell and thus deposits a thin adherent film during the core evaporation as shown below, a process that ends with hollow tubes. This property can be represented by the contact angle. The contact angle (wetting angle) between PEO solution (core 1, Table 2, hereinabove) drop and a cast PCL film as was visually measured is ~42°, while the contact angle between the water and PCL film is much higher (~90°), see FIGS. 5a-b. Hence, the PEO reduces the surface tension and provides the wetting of the solidified PCL. The inner deposited PEO film also provides a supplementary mechanical strength beyond the inherent strength of the PCL shell.

Example 3

The Relative Flow Rates of the Core and Shell Solutions can Determine the Fiber Diameter and the Formation of Hollow Fiber Experimental Results The Ratio Between the Flow Rates of the Core and Shell Solutions Plays an Important Role in Determining Both the Fiber Outer Diameter and Whether the Resulting Fiber is Hollow or Solid—

It is intuitively comprehensible that as the fiber gets thinner while the proportional core flow rate remains unchanged, the fiber will be solid since the core will fill the entire space within the tubes' walls. FIGS. 6a-c depict cross-sections of fibers made of same solutions with only difference in their electric conductivities. It is well known that the electric conductivity of the spun solution has an important influence on the resulting fiber diameter. As the conductivity of the solution increases, the fibers get thinner (S. A. Theron, E. Zussman, A. L. Yarin, Polymer 2004, 45, 2017). Here, the conductivity of the core solution was modified by addition of PBS (core 4, Table 2, hereinabove) but the flow rates ratio was not adjusted accordingly. As visualized, the thinner fibers (FIGS. 6 a and b), 2.1 m in diameter on average, are mostly solid while the thicker fibers (FIG. 6c), 6 µm in diameter on average, made of core solution with the regular low conductivity are hollow.

Example 4

Morphology of Shell

Experimental Results

Controlling the Shape of the Shell Morphology—

The morphology of the shell can be tailored according the applications requirements. For example the shell can be extensively porous thus creating a "breathing" tube, or on the other hand can be totally sealed thus forming a one-axial flow system. To produce "breathing" tubes the present inventors have used two approaches: In the first approach a higher percent of the volatile component (chloroform) for the shell solution (shell 2 in Table 2 hereinabove) was used, thus solidified even faster forming an extensively porous shell as shown in FIG. 7a. The second approach exploits the phase's behavior in polymer blend. Here a blend of PEG and PCL was used as the shell (shell 3 in Table 2 hereinabove). The phase separation during the solidification ended with highly porous tubes as presented in FIG. 7b.

Example 5

The Evaporation Process of the Core Polymer

Experimental Results

The Evaporation Process of the Core Polymer—

The evaporation of the PEO core solution occurs once the shell is assumed to be fully dry. The evaporation starts with the nucleation of bubbles which soon grow to the size of the inner diameter of the micro-tubes. Subsequently, the bubbles continue to grow longitudinally while being radially confined by the tube's wall leaving a thin film of polymeric solution. The nucleation of the bubbles occurs at many distant sites along the fibers consequently many slugs start to independently recede on both sides. The bubbles may nucleate at sites of defects or irregularities in the shell such as pores, holes, local thinning of the shell and more.

A schematic illustration of the solvent evaporation is shown in FIG. 8. The evaporation can take place at both the shell (region I) and the menisci (region II). In region I the solvent diffuses through the entire shell and evaporates. Region II describes the evaporation through the meniscus and the diffusion of the vapor to the outlet of the tubes. However, whenever the slugs are much longer than the tubes' diameter (as determined below), the evaporation through region II can be neglected. Since the vapor shall diffuse a long distance in order to reach the outlet, the concentration gradient along the vapor phase inside the tube is rather small slowing down the mass transport. On the other hand, due to the very large surface area of the micro-tubes and the negligible concentration of the solvent in the air surrounding the tubes, a large mass transport of solvent diffusing through the shell takes place in spite of the small diffusion coefficient $$D_I \approx 10^{-13} m^2/s$$

(Y. Peng, P. Y. Wu, Y. L. Yang, Journal of Chemical Physics 2003, 119, 8075). This transverse loss of mass causes the meniscus to recede at high velocity. A typical measured mean velocity of the meniscus is about $U \approx 50$ µm/sec. Accordingly, the Capillary number corresponding to this system is $$Ca = \mu U/\sigma \sim 10^{-3},$$

where $\mu$ and $\sigma$ are the viscosity of core 1 solution and the surface tension of water (www.knovel.com) respectively.

For region I, knowing the diffusivity of the solvent across the shell, the amount of solvent evaporated can be calculated and the meniscus receding evolution can be estimated by the following mass balance equation:

$$\frac{dm}{dt} = 2\pi a X D_I \frac{dc}{dr}\bigg|_{r=a} = c_1 \pi a^2 \frac{dX}{dt} \qquad \text{Equation (1)}$$

where the middle term describes the diffusion through the shell and the right hand side describes the movement of the meniscus where X is the half length of the slug. Assuming steady state, the evolution of the meniscus X with time t is $$X = X_0 e^{-t/t_I} \qquad \text{Equation (2)}$$

where $$t_I = \frac{c_1 a^2 \ln(b/a)}{2 D_I (c_1 - c_2)}$$

$X_0$ is the initial half length of the slug, a and b are the inner and outer diameter of the tube, and $c_1$ and $c_2$ are the concentration of the solvent at the inner and the outer sides of the micro-tubes respectively.

For region II, assuming the concentration profile of the vapor is determined by one-dimensional linear diffusion process, the evolution of the meniscus as function of time is given as:

$$\frac{(L-X)}{(L-X_0)} = \sqrt{1 + \frac{t}{t_{II}}} \qquad \text{Equation (3)}$$

where $$t_{II} = \frac{c_1 (L-X_0)^2}{2 D_{II}(c_s - Hc_s)},$$

$c_s$ is the saturated vapor density of the solvent, H is the relative humidity, $D_{II}$ is the diffusion coefficient of the solvent vapor in the gas phase, and L is the distance from the center of the slug to the outlet.

It appears that for a short slug ($X_0$ in the order of tenths of microns) the characteristic times of the evaporation from region I and II are of the same order, for example when $X_0 = 50$ µm $$t_{II} \approx c_1 X_0^2 / c_s D_{II} = 12 s$$

and $$t_I \approx a^2 / D_I = 10 s$$

($c_1 = 1000$ kg/m$^3$, $c_s = 0.023$ kg/m$^3$, and $D_{II} \sim 10^{-5}$ m$^2$/s) (www.epa.gov/athens/learn2model/part-two/onsite/estdiffusion.htm). However, for a longer slug, $t_{II}$ is exceeding several minutes while $t_I$ is still in the order of tenths of seconds. For example for $X_0 = 500$ µm, $t_{II} \sim 20$ minutes. Sequences of video frames showing the receding of several slugs during the evaporation process in a few experiments are presented in FIGS. 9a-d and 9e-h. The experimental results showing the displacement of the meniscus as a function of time together with the calculated values are presented in FIG. 9i. For both tests i and ii good agreement with equation (2) is found, namely massive evaporation occurs through the shell. However, for test iii where the slug is short, the mass flux evaporated from the meniscus can not be ignored, thus the evolution of the meniscus X with time is calculated as a linear combination of equations (2) and (3), resulting in a good agreement with the experimental results.

As was argued before, the meniscus moves due to the loss of mass through the shell leaving behind a thin but macroscopic film of PEO solution with thickness in the order of $a \cdot Ca^{2/3} \sim 100$ nm (J. Bico, D. Quere, J. Fluid. Mech. 2002, 467, 101). By the end of the evaporation a layer of polymer is deposited forming a wavy pattern as shown in FIGS. 10a-b. The diffusion of the water/ethanol mixture through the shell is slow due to the relative hydrophobicity of the PCL. Yet the diffusion is still available due to the possible absorption of water at the carbonyl sites of the ester groups in PCL via hydrogen bonding as was already demonstrated by Peng et al. (Y. Peng, P. Y. Wu, Y. L. Yang, Journal of Chemical Physics 2003, 119, 8075) that detected the diffusion of water in PCL film. In the present case, besides the porosity of the shell, the presence of the PEO encourages the absorption of the water and the diffusion, since the PEO easily wets the surface and makes the surface accessible for the water/ethanol molecules. In addition, the PEO can be dissolved in DMF up to a certain level and thus may penetrate into the PCL film at least a few nanometers before final solidification. This also enhances the penetration of the water and ethanol molecules and affects the inner surface morphology.

Example 6

Filling of Microtubes with Liquid

Experimental Results
Filling of Electrospun Microtubes with Liquid—
An additional evidence for the formation of hollow fibers which has also an important practical consequence is the filling of these micro-tubes. Drops of silicon oil were placed onto the micro-tubes non-woven mat. The silicon drop easily wets the surface was immediately sucked by capillary forces through the porous shell and a progressive movement of a meniscus was observed by LM as can be seen in FIGS. 11a-d. Experimental results of the filling process show that the meniscus progresses as nearly a linear function of time and the whole process takes only a few seconds (FIG. 11e).

It should be emphasized that in contrast to regular capillary filling experiment where the drop is placed at the entrance of the tube, here the drop was placed on top of the micro-tube mat and the penetration was through the shell pores. As a consequence, the pressure drop across the tube was uneven. Therefore, the measured filling rate varied between the tubes and the filling rates do not follow the Washburn's theory (E. W. Washburn, Physical Review 1921, 17, 273) for which progression of the meniscus as function of square root of time would have been expected.

Example 7

Evaluation of Electrospun Microtubes

Experimental Results
Table 3, hereinbelow, presents the co-electrospinning results of different combinations of core/shell polymer solutions. The results refer to the ability to form tubes and distinguish between three cases: (a) perfect tube, (b) good tube, and collapsed tube. Perfect tube situation is considered when very small variations in the tube geometrical parameters were observed (e.g., the inner diameter varies at the most +/−0.1 m). Good tube situation is related to tubes which were stable however, variation in the geometry was observed (e.g., the inner diameter varies at the most +/−2 μm). Collapsed situation refer to a complete destroy morphology of the tube. Solid fiber is referred to the situation when co-electrospinning results in a solid core/shell fiber unlike a tube.

TABLE 3

Electrospun micro-fibers

| Sys No. | | System | Flow rates (ml/hr) | Relative Humidity (%) | Results |
|---|---|---|---|---|---|
| 1 | Shell 1 | 10% PCL in $CHCl_3$/DMF 80:20 | 4 | 62 | Good tubes |
|  | Core 1 | 4% PEO in $H_2O$/EtOH 60:40 | 0.5 | | |
| 2 | Shell 1 | 10% PCL in $CHCl_3$/DMF 80:20 | 3.5 | 59 | Perfect tubes |
|  | core | 6% PEO in $H_2O$/EtOH 60:40 | 0.5 | | |
| 3 | Shell 1 | 10% PCL in $CHCl_3$/DMF 80:20 | 4 | 30 | Collapsed fibers |
|  | core | 8% PEO in $H_2O$/EtOH 60:40 | 0.5-1 | | |
| 4 | Shell 1 | 10% PCL in $CHCl_3$/DMF 80:20 | 4 | 62 | Good tubes, |
|  | core | 4% PEO in $H_2O$/EtOH 60:40 | 0.5 | | |
| 5 | Shell 1 | 10% PCL in $CHCl_3$/DMF 80:20 | 4 | 40 | Collapsed fibers |
|  | core | 4% PEO in $H_2O$ | 0.5-1 | | |
| 6 | shell | 10% PCL + 1% PEG 6K in CHCl3/DMF 90:10 | 4 | 56 | Collapsed fibers. PEG 6k Mw was blended with the shell polymer to enhance its porosity |
|  | core | 4% PEO in $H_2O$/EtOH 60:40 | 0.5 | | |
| 9 | shell | 8% PCL in $CHCl_3$ | 4 | 44 | Solid round fibers. |
|  | core | 4% PEO in H2O/EtOH 60:40 | 0.3 | | |
| 10 | shell | 8% PCL in $CHCl_3$ | 4 | 45 | Solid round fibers |
|  | core | 7% PEO in $H_2O$ | 0.3 | | |

TABLE 3-continued

Electrospun micro-fibers

| Sys No. | | System | Flow rates (ml/hr) | Relative Humidity (%) | Results |
|---|---|---|---|---|---|
| 11 | shell | 9% PCL in CHCl$_3$/DMSO 90:10 | 3.5 | 51 | Good tubes. Highly porous shell surface (pore size 0.3-1 μm). |
| | core | 7% PEO in H$_2$O | 0.5 | | |

Table 3: Shell Polymer: PCL 80 kDa, Core polymer PEO 600 kDa. Ambient Temperature range was 22-25° C.

Example 8

Development of Artificial Vascular Microfluidic Networks

Here the present inventors report the development of microfluidic networks of a biocompatible polymer. Microfluidic were produced by co-electrospinning of polymer solutions. The network resembling a capillary bed. The network used in this study has a total surface area of about 40 mm$^2$. The inner diameters of the vessels range from 7 μm to 20 μm with wall thickness of about 0.5 μm. An overview of a microfluidic network is presented in FIG. 12a. The inlet and outlet of the network are connected with a Teflon medical tube (SCI Scientific Commodities Inc., I.D. 0.036", and 0.066" O.D.). The network was slightly inserted into the Teflon tube and sealed with an adhesive (Pattex N27, Henkel adhesives, Spain). Images of the cross-section of electrospun microfluidic network are presented in FIG. 12b. The microtubes are oriented and attached together. The tube were made by co-electrospinning of shell 1 and core 1 solutions (see Table 2, hereinabove).

Flow test was conducted with these microfluidics constructs as follow: blood drop was diluted with an heparin solution (heparin concentration (100 units/ml), 1:1 blood). A micro drop (0.2 ml) was located at the inlet of the construct. A capillary flow was observed under an optical microscope (see FIG. 13). Blood red cells were moving in a typical speed of 20 μm/second.

Altogether, these results clearly demonstrate the use of the microtube of the invention for blood flow.

CONCLUSIONS

The fabrication of biocompatible and biodegradable polymeric microtubes in a one step procedure by co-electrospinning has been presented. These microtubes serve as microfluidic systems which may offer many bio-medical applications. Few conditions are required in order to achieve tubes by this approach:

(1) Fast solidification of the shell solution;
(2) Good wetting of the shell by the core solution. This can be achieved using a core solution consisting of a non-solvent to the shell polymer. Thus a film can be instantaneously formed at the interface due to the precipitation of the shell polymer. This film assists the stabilization of the co-electrospinning process and the formation of tubes with uniform and strong walls.
(3) It is recommended to use a viscoelastic polymeric core solution in order to gain a stabilized co-electrospinning process and deposition of significant polymeric film on the inner surface of the shell. This provides additional mechanical strength to the tubes' walls;
(4) The shell to core flow rates ratio should be chosen according to the diameter of the resulting fibers in order to achieve hollow structure.

The evaporation process of the core solvent occurred by both the diffusion of the solvent through the large area of the shell and evaporation through the meniscus. The large mass loss induced the fast receding of the slugs accompanied by deposition of PEO (e.g., core polymer) film. Without being bound by any theory, it is suggested that although the PCL shell is relatively hydrophobic the diffusion of the water and ethanol was encouraged by the porous character of the shell and the presence of the PEO which permitted the penetration of the water/ethanol molecules. The filling of these microtubes was also demonstrated showing that silicon oil and blood were rapidly sucked into the tubes by capillary forces. The method of the invention depends on the stability of the co-electrospinning step which is affected by many factors such as miscibility or non-miscibility of the pair of solutions, viscosity ratio, viscoelastic relaxation time ratio, relative permittivities and conductivities ratios, interfacial tension, the electric field strength as well as the degree of protrusion of the core nozzle outside of the shell nozzle (Reznik S N, et al., 2006).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

REFERENCES

Additional References are Cited in Text

1. D. H. Reneker, A. L. Yarin, E. Zussman, H. Xu, Advances in Applied Mechanics 2006, 40.
2. S. Ramakrishna, K. Fujihara, W.-e. Teo, Lim, T. C., Z. Ma, An Introduction to Electrospinning and Nanofibers, 1 ed., World Scientific Publishing Company, 2005.

3. D. Li, Y. N. Xia, Advanced Materials 2004, 16, 1151.
4. M. Bognitzki, H. Hou, M. Ishaque, T. Frese, M. Hellwig, S. C., A. Schaper, J.
   H. Wendorff, A. Greiner, Adv. Mater. 2000, 12, 637.
5. R. A. Caruso, J. H. Schattka, A. Greiner, Adv. Mater. 2001, 13, 1577.
6. Z. Sun, E. Zussman, A. L. Yarin, J. H. Wendorff, A. Greiner, Adv. Mater. 2003, 15, 1929.
7. J. H. Yu, S. V. Fridrikh, G. C. Rutledge, Adv. Mater. 2004, 16, 1562.
8. Z. M. Huang, C. L. He, A. Yang, Y. Zhang, X. J. Han, J. Yin, Q. Wu, J. Biomedical Materials Research, Part A 2006, 77A, 169.
9. H. Jiang, Y. Hu, Y. Li, P. Zhao, K. Zhu, W. Chen, J. Control. Release 2005, 108, 237.
10. Y. Z. Zhang, X. Wang, C. T. Lim, S. Ramakrishna, Biomacromolecules 2006, 7, 1049.
11. D. Li, Y. Xia, Nano Letters 2004, 4, 933.
12. D. Li, J. T. McCann, Y. Xia, Small 2005, 1, 83.
13. E. Zussman, A. L. Yarin, V. Bazilevsky, R. Avrahami, M. Feldman, Adv. Mater. 2006, 18, 348.
14. S. N. Reznik, A. L. Yarin, E. Zussman, L. Bercovici, Physics of Fluids 2006, 18, 1.
15. D. Li, J. T. McCann, Y. Xia, J. Am. Ceram. Soc. 2006, 89, 1861.
16. I. G. Loscertales, A. Barrero, I. Guerrero, R. Cortijo, M. Marquez, A. M. Ganan-Calvo, Science 2002, 295, 1695.
17. I. G. Loscertales, A. Barrero, M. Marquez, R. Spretz, R. Velarde-Ortiz, G. Larsen, Journal of the American Chemical Society 2004, 126, 5376.

The invention claimed is:

1. A method of producing a microtube, the method comprising: co-electrospinning two polymeric solutions through co-axial capillaries to thereby produce the microtube, wherein a first polymeric solution of said two polymeric solutions is for forming a shell of the microtube and a second polymeric solution of said two polymeric solutions is for forming a coat over an internal surface of said shell, said first polymeric solution is selected solidifying faster than said second polymeric solution and a solvent of said second polymeric solution is selected incapable of dissolving said first polymeric solution, wherein a thickness of said shell is from about 100 nm to about 20 micrometer, and wherein an internal diameter of the microtube is from about 50 nm to about 50 micrometer.

2. The method of claim 1, wherein said co-electrospinning comprises a one-step co-electrospinning for producing the microtube.

3. The method of claim 1, wherein a solvent of said first polymeric solution evaporates faster than a solvent of said second polymeric solution.

4. The method of claim 1, wherein said electrospinning is effected using a rotating collector.

5. The method of claim 1, wherein a solvent of said second polymeric solution is capable of evaporating through said internal surface of said shell.

6. The method of claim 1, wherein said second polymeric solution is capable of wetting said internal surface of said shell.

7. The method of claim 1, wherein a thickness of said shell is from about 200 nm to about 10 micrometer.

8. The method of claim 1, wherein an internal diameter of the microtube is from about 50 nm to about 20 micrometer.

9. The method of claim 1, wherein the method of claim 1, wherein said second polymeric solution comprises a surface active polymer.

10. The method of claim 1, wherein said first polymeric solution comprises polyethylene glycol (PEG).

11. The method of claim 1, wherein said shell comprises pores.

12. The method of claim 1, wherein said microtube is filled with a liquid.

13. The method of claim 12, wherein said liquid is blood.

14. The method of claim 1, wherein said first and said second polymeric solutions are biocompatible.

15. The method of claim 1, wherein said first polymeric solution comprises a polymer selected from the group consisting of poly (e-caprolactone) (PCL), polyamide, poly (siloxane), poly(silicone), poly(ethylene), poly(vinyl pyrrolidone), poly(2-hydroxy ethylmethacrylate), poly(N-vinyl pyrrolidone), poly(methyl methacrylate), poly(vinyl alcohol), poly(acrylic acid), poly(vinyl acetate), polyacrylamide, poly(ethylene-co-vinyl acetate), poly(ethylene glycol), poly (methacrylic acid), polylactide, polyglycolide, poly(lactide-coglycolide), polyanhydride, polyorthoester, poly(carbonate), poly(acrylo nitrile), poly(ethylene oxide), polyaniline, polyvinyl carbazole, polystyrene, poly(vinyl phenol), polyhydroxyacid, poly(caprolactone), polyanhydride, polyhydroxyalkanoate, polyurethane, collagen, albumin, alginate, chitosan, starch and hyaluronic acid.

16. The method of claim 1, wherein said second polymeric solution comprises a polymer selected from the group consisting of poly(acrylic acid), poly(vinyl acetate), polyacrylamide, poly(ethylene-co-vinyl acetate), poly(ethylene glycol), poly(methacrylic acid), polylactide polyglycolide, poly(lactide-coglycolide), polyanhydride, polyorthoester, poly(carbonate), poly(ethylene oxide), polyaniline, polyvinyl carbazole, polystyrene, poly(vinyl phenol), polyhydroxyacid, alginate, starch and hyaluronic acid.

* * * * *